US010856904B2

(12) United States Patent
Gerber

(10) Patent No.: US 10,856,904 B2
(45) Date of Patent: Dec. 8, 2020

(54) FLEXIBLE INTRODUCER

(75) Inventor: Martin T. Gerber, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 3050 days.

(21) Appl. No.: 11/606,627

(22) Filed: Nov. 30, 2006

(65) Prior Publication Data
US 2008/0132933 A1  Jun. 5, 2008

(51) Int. Cl.
| A61M 29/00 | (2006.01) |
| A61B 17/34 | (2006.01) |
| A61N 1/05  | (2006.01) |
| A61B 17/00 | (2006.01) |
| A61M 25/06 | (2006.01) |
| A61B 90/00 | (2016.01) |

(52) U.S. Cl.
CPC ........ *A61B 17/3468* (2013.01); *A61N 1/0534* (2013.01); *A61N 1/0551* (2013.01); *A61B 17/3401* (2013.01); *A61B 17/3417* (2013.01); *A61B 17/3421* (2013.01); *A61B 2017/00292* (2013.01); *A61B 2090/3937* (2016.02); *A61M 25/0662* (2013.01); *A61N 1/0558* (2013.01)

(58) Field of Classification Search
USPC ......... 607/115–125, 145, 147; 600/139, 143; 604/524–525, 530
See application file for complete search history.

(56) References Cited

U.S. PATENT DOCUMENTS

| 4,906,230 | A  |   | 3/1990  | Maloney et al. |
| 5,441,483 | A  | * | 8/1995  | Avitall ...................... 604/95.05 |
| 6,419,674 | B1 | * | 7/2002  | Bowser .................. A61N 1/057 606/45 |
| 6,505,075 | B1 |   | 1/2003  | Weiner |
| 6,749,560 | B1 | * | 6/2004  | Konstorum et al. .......... 600/143 |
| 6,847,849 | B2 |   | 1/2005  | Mamo et al. |
| 7,044,921 | B2 |   | 5/2006  | Asmus et al. |
| 2001/0044624 | A1 |   | 11/2001 | Seraj et al. |
| 2002/0147485 | A1 | * | 10/2002 | Mamo et al. ................. 607/116 |
| 2002/0173785 | A1 | * | 11/2002 | Spear ................. A61B 18/1492 606/41 |

(Continued)

FOREIGN PATENT DOCUMENTS

| DE | 41 04 092 A1   | 8/1991 |
| DE | 198 54 297 A1  | 5/2000 |

(Continued)

OTHER PUBLICATIONS

"Medtronic Neurostimulation System for the Treatment of Chronic Migraine Headache," System Manual, Medtronic, Inc., 2006, (47 pages).

(Continued)

*Primary Examiner* — Erica S Lee
(74) *Attorney, Agent, or Firm* — Shumaker & Sieffert, P.A.

(57) ABSTRACT

An introducer for facilitating implantation of a therapy element into a patient defines a lumen configured to receive the therapy element. At least a portion of the introducer is configured to preferentially flex in at least a first direction over at least a second direction. That is, at least a portion of the introducer is predisposed to bend in a particular direction. In some embodiments, the introducer may also resist bending in one or more directions.

26 Claims, 13 Drawing Sheets

(56) References Cited

U.S. PATENT DOCUMENTS

| | | | | |
|---|---|---|---|---|
| 2003/0225425 A1* | 12/2003 | Kupiecki | ............... | A61B 17/11 606/153 |
| 2004/0193140 A1* | 9/2004 | Griffin et al. | ................. | 604/524 |
| 2004/0210245 A1 | 10/2004 | Erickson et al. | | |
| 2005/0043682 A1* | 2/2005 | Kucklick | ........... | A61B 17/3421 604/164.09 |
| 2005/0049664 A1* | 3/2005 | Harris | ................ | A61B 17/3401 607/115 |
| 2005/0228479 A1* | 10/2005 | Pavcnik et al. | .............. | 623/1.11 |
| 2008/0009823 A1* | 1/2008 | McKay | ............. | A61B 17/7044 604/500 |

FOREIGN PATENT DOCUMENTS

| | | | |
|---|---|---|---|
| WO | WO 00/76404 | A2 | 12/2000 |
| WO | 2005/023359 | A1 | 3/2005 |
| WO | 2006/066009 | | 6/2006 |

OTHER PUBLICATIONS

Written Opinion of the International Preliminary Examining Authority for corresponding patent application No. PCT/US2007/001941, dated Feb. 16, 2009, 6 pages.

Reply to Written Opinion for corresponding patent application No. PCT/US2007/001941, filed Jul. 15, 2008, 12 pages.

Reply to Written Opinion for corresponding patent application No. PCT/US2007/001941, filed Mar. 16, 2009, 4 pages.

Notification of Transmittal of the International Preliminary Report on Patentability for corresponding patent application No. PCT/US2007/001941, dated Apr. 6, 2009, 10 pages.

Notification of Transmittal of the International Search Report and the Written Opinion of the International Searching Authority for corresponding patent application No. PCT/US2007/001941, dated Aug. 17, 2007, 15 pages.

* cited by examiner

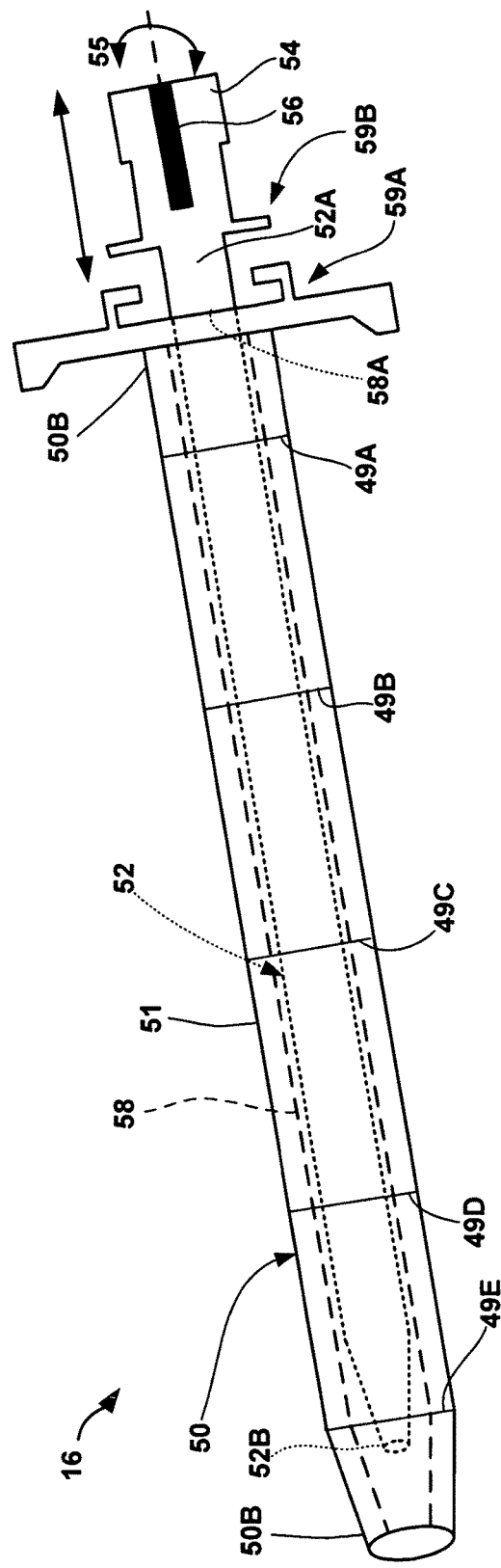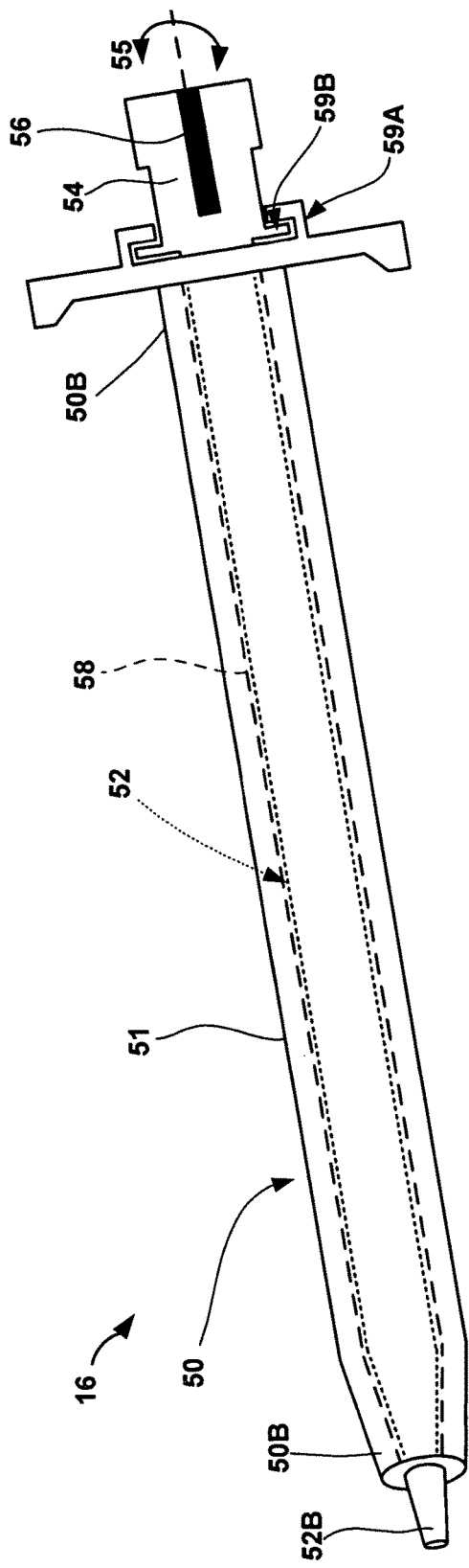
FIG. 3A
FIG. 3B

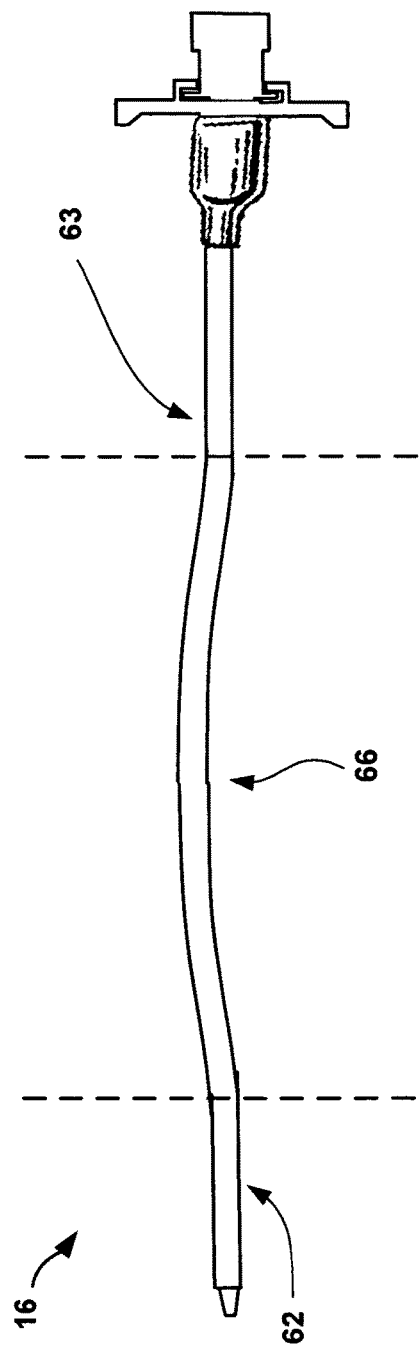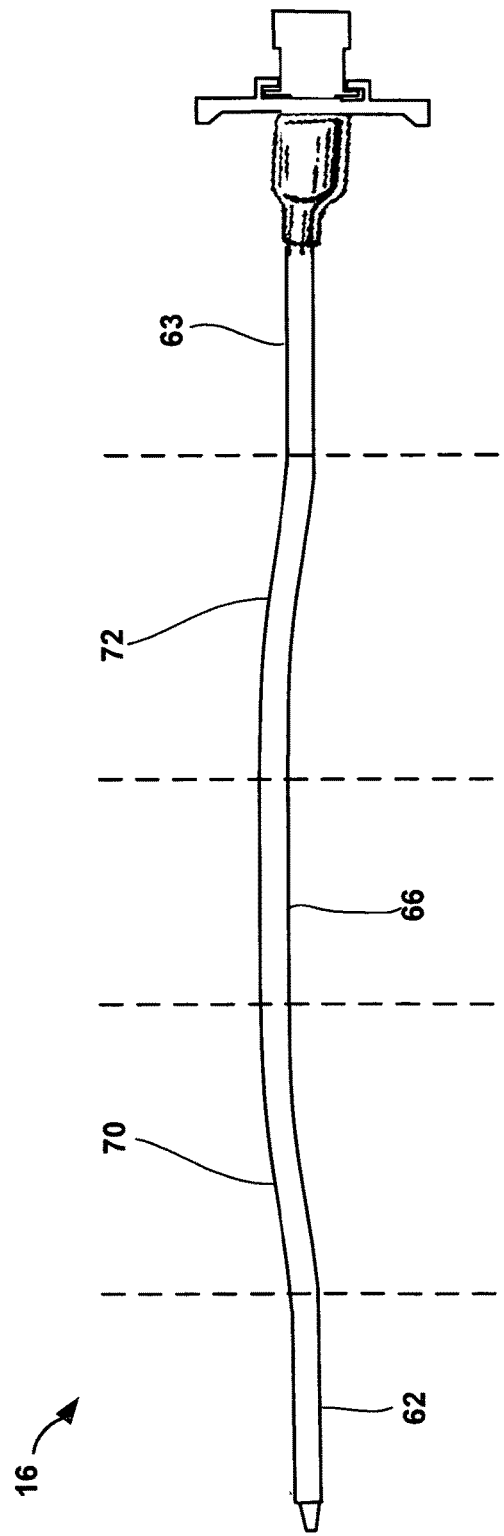
FIG. 7
FIG. 8

FLEXIBLE INTRODUCER

TECHNICAL FIELD

The invention relates to implantable medical devices and, more particularly, to a device for aiding the implantation of an implantable medical device.

BACKGROUND

Neurostimulation systems may be used to deliver neurostimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, or obesity. A neurostimulation system typically includes one or more neurostimulation leads coupled to a neurostimulator.

The neurostimulation lead may be percutaneously or surgically implanted in a patient on a temporary or permanent basis such that at least one stimulation electrode is positioned proximate to a target tissue site. The target tissue site may be, for example, a spinal cord, occipital nerve, pelvic nerve, pudendal nerve, stomach, or within a brain of a patient. The one or more electrodes located proximate to the target tissue site may deliver neurostimulation therapy to the target tissue site in the form of electrical pulses or may sense physiological parameters of the patient.

Electrical stimulation of a peripheral nerve, such as stimulation of an occipital nerve, may be used to induce paresthesia. Occipital nerves exit the spinal cord at the cervical region, extend upward and towards the sides of the head, and pass through muscle and fascia to the scalp. Pain caused by an occipital nerve, e.g., occipital neuralgia, may be treated by implanting a lead proximate to the occipital nerve to deliver stimulation therapy.

In some electrical stimulation applications, percutaneous leads are often preferred over surgically implanted leads because percutaneously implanted leads are implanted in a less invasive manner. For example, in order to implant a percutaneous lead transversely across the occipital nerve an incision may be made to ease the introduction of an introducer, such as a percutaneous needle. The introducer is advanced through subcutaneous tissue to a position over (superior to) the occipital nerve that is causing the pain. When the introducer is in position above the target occipital nerve, the lead is passed through the introducer needle until the lead is also in position above the target occipital nerve. The introducer can then be removed from the patient leaving the lead implanted above the occipital nerve.

SUMMARY

In general, the invention is directed to an introducer for facilitating implantation of a therapy element into a patient. The introducer has an elongated body that defines a lumen configured to receive a therapy element, such as a lead body carrying one or more electrodes or a fluid delivery conduit, e.g., a catheter, to an implant site within the patient. At least a portion of the introducer is configured to preferentially flex in at least one direction over at least one other direction. That is, at least a portion of the introducer is predisposed to flex more easily in a particular direction to help prevent the introducer from inadvertently flexing in a direction that may damage tissue, and possibly harm the patient, during implantation of the therapy element. The flexibility of at least a portion of the introducer enables the introducer to change shape (e.g., from substantially straight to curvilinear, or between various curvilinear shapes) and adapt to certain environments in order to allow a clinician to advance the introducer to an implant site with more precision. For example, a clinician may manipulate the introducer to conform to an anatomical structure of a patient, e.g., a transverse contour of the neck of a patient, to reduce trauma caused during implantation of the therapy element within the patient.

In embodiments, the introducer may be configured to preferentially flex in at least one direction over at least one other direction by forming grooves, such as striations, channels, and the like, into at least a portion of the introducer. In other embodiments, the introducer may have a shape that predisposes the introducer to be more easily bendable in at least one direction than at least one other direction. In yet other embodiments, the introducer may comprise an inner wall having a varying thickness that enables the introducer the preferentially flex in at least one direction.

In one embodiment, the invention is directed to an apparatus to facilitate implantation of a therapy element into tissue of a patient. The apparatus comprises an elongated body, an inner lumen defined by the elongated body and configured to receive the therapy element, wherein at least a portion of the elongated body is configured to preferentially flex in at least a first direction over at least a second direction.

In another embodiment, the invention is directed to a kit to facilitate implantation of a therapy element into a patient. The kit comprises a dilator, and a sheath defining an inner lumen configured to interchangeably receive the dilator and the therapy element. At least one of the dilator or the sheath comprises a flexible portion configured to flex in a first direction and resist flexing in a second direction.

In a further embodiment, the invention is directed to a method comprising inserting an introducer into a patient, the introducer comprising a lumen configured to receive a therapy element, wherein at least a portion of the introducer is configured to preferentially flex in at least a first direction over at least a second direction. The method further comprises advancing the introducer to a target tissue site within the patient, and manipulating the portion of the introducer to flex in the first direction.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 3A and 3B are schematic diagrams illustrating an example introducer for use in the therapy system that is configured to flex more easily in a direction than at least one other direction.

FIGS. 5A-9 are schematic diagrams illustrating example configurations of introducers that have been manipulated to bend in predisposed directions.

FIGS. 10A-12B illustrate various configurations of introducers that preferentially flex in at least one direction over at least one other direction.

DETAILED DESCRIPTION

Figure 1:
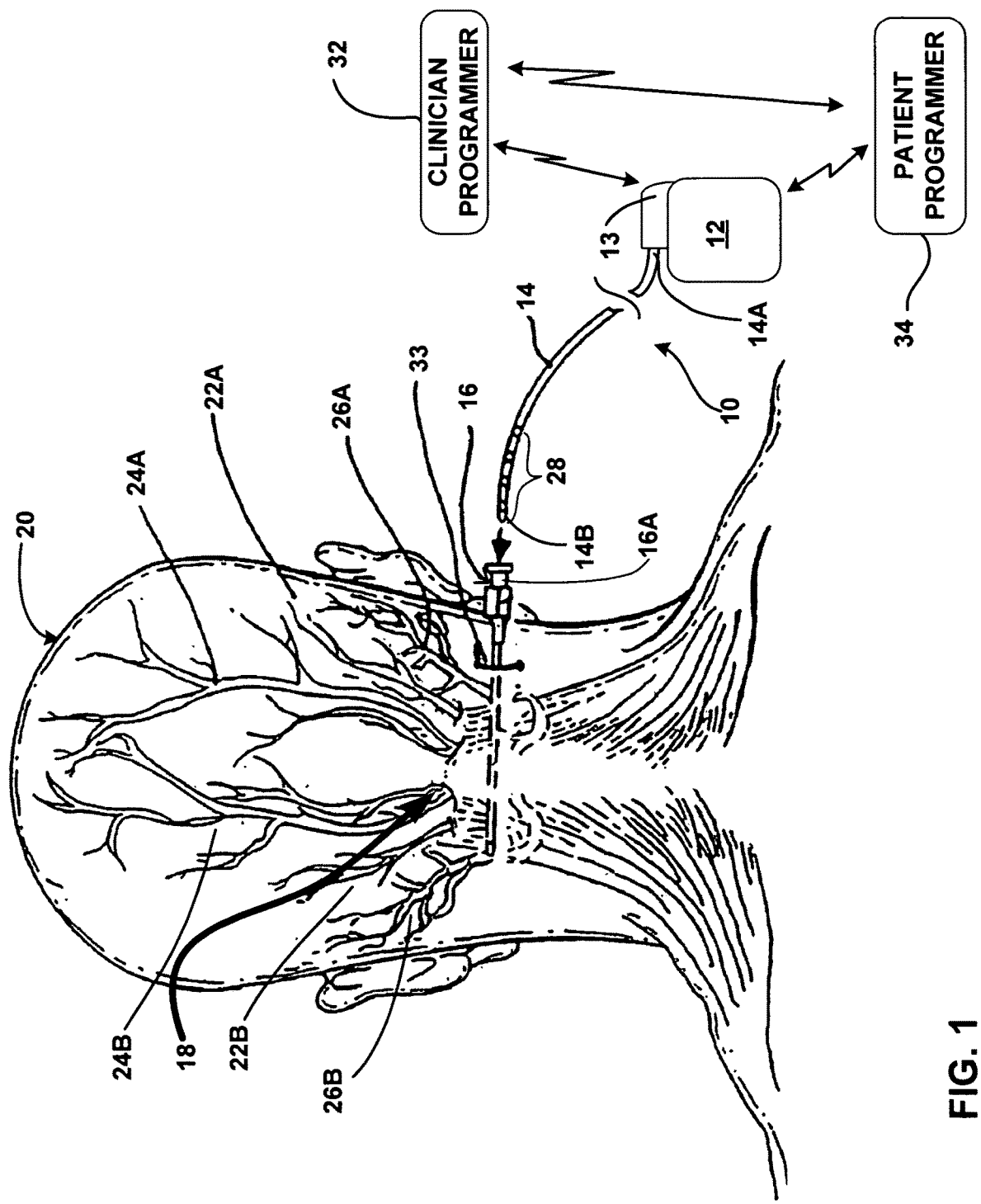
FIG. 1 illustrates a therapy system, which includes an introducer for facilitating implantation of a therapy element into a patient.

The present invention relates to an introducer for facilitating implantation of a therapy element, such as a lead body carrying one or more electrodes or a fluid delivery conduit, into a patient. The introducer defines a lumen configured to receive the therapy element, through which the therapy element may be advanced to reach an implant site (e.g., a target tissue site) within the patient. At least a portion of the introducer is configured preferentially flex in at least one direction over at least one other direction. That is, the introducer may be predisposed to bend in a particular direction, and in some embodiments, the introducer may resist bending in other directions. The preferentially flexibility may be achieved by any suitable technique. For example, grooves (e.g., striations, channels, and the like) may be formed in the introducer to help define flexible portions of the introducer that flex in a predisposed direction. As other examples, the cross-sectional shape of the introducer may help define one or more portions that preferentially flex in at least one direction or the introducer may comprise an inner wall exhibiting varying thickness.

The preferential flexibility of the introducer may allow a clinician to more easily, and without substantially damaging surrounding tissue, advance the introducer to an implant site than would be possible with a straight needle or a needle having a predefined curved portion. For example, a clinician may manipulate the introducer to conform to an anatomical structure of a patient, e.g., a transverse contour of the neck of a patient, to reduce trauma caused during implantation of the therapy element within the patient. The introducer, however, may be configured to be manipulated to conform to many anatomical structures, particularly structures having an irregular shape or structures that vary in shape from one patient to another, such as a facial structure above or below the eye.

The introducer may be used to facilitate implantation of therapy elements into a patient for different therapeutic applications. For example, the introducer may be used to facilitate implantation of an electrical stimulation lead or lead extension that is used to deliver electrical stimulation to a target stimulation site and/or sense one or more physiological parameters, e.g., blood pressure, temperature, or electrical activity, of a patient. In another embodiment, the introducer may facilitate implantation of a fluid delivery conduit, such as a catheter, which is placed to deliver a fluid, such as pharmaceutical agents, insulin, pain relieving agents, gene therapy agents or the like from a fluid delivery device, such as a fluid reservoir and/or pump, to a target tissue site in a patient. Thus, in some embodiments, "therapy" may include stimulation therapy, sensing or monitoring of one or more physiological parameters, fluid delivery, and the like. "Target tissue site" refers generally to the target site for implantation of an elongated member, regardless of the type of therapy. The introducer may be used to facilitate implantation of any therapy element that is used to deliver therapy to a site in a patient. For purposes of illustration and brevity, however, the disclosure refers to the implantation of a neurostimulation lead.

FIG. 1 is a schematic diagram illustrating a therapy system 10 including an electrical stimulator 12 coupled to implantable medical lead 14. Lead 14 is aligned to be inserted into introducer 16 for implantation proximate to a target tissue site 18 (which in the embodiment shown in FIG. 1 is a target stimulation site) within patient 20 for stimulation of one or more occipital nerves. In the embodiment shown in FIG. 1, introducer 16 defines an insertion path from a scalp or epidermis of patient 20 to target tissue site 18. In the example shown in FIG. 1, target tissue site 18 is proximate to at least one of lesser occipital nerves 22A and 22B (collectively referred to as "lesser occipital nerves 22"), greater occipital nerves 24A and 24B (collectively referred to as "greater occipital nerves 24"), or third occipital nerves 26A and 26B (collectively referred to as "third occipital nerves 26"). In alternate embodiments, lead 14 may be implanted proximate to one or more other peripheral nerves proximate to occipital nerves 22, 24, and 26 of patient 20, such as nerves branching from occipital nerves 22, 24, or 26 or a trigeminal nerve. Stimulation of occipital nerves 22, 24, and 26 or a trigeminal nerve may help alleviate pain associated with, for example, chronic migraines, cervicogenic headaches, occipital neuralgia or trigeminal neuralgia.

In the embodiment shown in FIG. 1, electrical stimulator 12 is a neurostimulator that is either implantable or external. For example, neurostimulator 12 may be subcutaneously implanted in the body of a patient, e.g., within a subcutaneous pocket in a chest cavity, lower back, lower abdomen, or buttocks of patient 20. Neurostimulator 12 provides a programmable stimulation signal e.g., in the form of electrical pulses or substantially continuous-time signals that is delivered to target tissue site 18 by implantable medical lead 14, and more particularly, via one or more stimulation electrodes 28 carried by lead 14. In some embodiments, neurostimulator 12 may be coupled to two or more leads, e.g., for bilateral or multi-lateral stimulation. Neurostimulator 12 may also be referred to as a pulse generator. In some embodiments, lead 14 may also carry one or more sense electrodes to permit neurostimulator 12 to sense electrical signals from target tissue site 18.

Proximal end 14A of lead 14 may be both electrically and mechanically coupled to connector 13 of neurostimulator 12 either directly or indirectly, e.g., via a lead extension. In particular, conductors disposed within a lead body of lead 14 electrically connect stimulation electrodes 28, and sense electrodes, if present, located adjacent to distal end 14B of lead 14 to neurostimulator 12. Proximal end 14A of lead 14 may include electrical contacts that correspond to each of the conductors that are electrically connected to electrodes 28, where the electrical contacts electrically couple electrodes 28 to neurostimulator 22 via connector 13.

Accurate placement of a therapy element may affect the success of therapy delivered by therapy system 10. For example, if lead 14 is located too deep, i.e., anterior in the subcutaneous tissue, patient 20 may experience muscle contractions, grabbing sensations, or burning. Thus, substantial accuracy and precision is desirable when implanting lead 14 proximate to target tissue site 18 proximate to occipital nerves 22, 24, and 26. In addition, lead 14 may include one or more fixation elements (shown in FIG. 2) to help substantially fix lead 14 proximate to target tissue site 18. Substantially fixing lead 14 to surrounding tissue may help prevent lead 14 from migrating from target tissue site 18 following implantation, which may ultimately help avoid harmful effects that may result from a migrating lead 14. The fixation elements may be any suitable actively or passively deployed fixation elements that helps prevent migration of lead 14, such as, but not limited to, one or more tines, barbs, hooks, wire-like elements, adhesives, balloon-like fixation elements, tissue receiving cavities, pinning fixation elements, collapsible or expandable fixation structures, and the like.

Due to the location of an implanted lead 14 on the back of the neck of patient 20, care should be taken to avoid inadvertently advancing the introducer into or through the scalp of the patient. For these reasons, an introducer 16 that is configured to be manipulated to conform to an anatomical structure, such as the back of the neck of patient 20, may be advantageous. In particular, an introducer 16 designed to preferentially flex in one direction than another may facilitate manipulation into a shape that conforms to anatomical structure of patient 20. To facilitate manipulation, i.e., being more flexible in one direction than another direction, grooves, such as striations, channels, and the like, may be formed in at least portions of introducer 16 to help define one or more portions that exhibit preferential flexibility. Other features are also possible to promote bending or flexing in one direction over another.

Introducer 16 extends between proximal end 16A and distal end 16B and defines an inner lumen (not shown in FIG. 1) configured to receive lead 14. As described in further detail below, at least a portion of introducer 16 is configured to preferentially flex (or bend) in at least one direction over at least one other direction to facilitate implantation of medical lead 14 at target tissue site 18. Thus, in the embodiment of FIG. 1, introducer 16 is predisposed to bend in a particular direction to allow a clinician to manipulate introducer 16 to conform to the transverse contour of the back of the neck of patient 20 when lead 14 is implanted near the back of the head of patient 20. "Bend" and "flex" are used interchangeably throughout the present disclosure, and generally refer to manipulating an object, i.e., introducer 16, from an initial shape, such as a substantially straight shape, into another shape, such as a curvilinear or angular shape. In some embodiments, introducer 16 may resist bending in some directions. Thus, a clinician can more accurately, and without substantially damaging surrounding tissue, advance introducer 16 to target tissue site 18 than would be possible with a substantially straight introducer or an introducer having a pre-curved shape at or very near a distal end. In particular, the possibility of extending introducer 16 into or through the scalp of patient 20 is minimized or substantially eliminated because introducer 16 can be manipulated to conform to the neck or head of patient 20, and may be configured to resist bending in unwanted directions (e.g., toward the scalp of epidermis of patient 20) while being advanced through tissue to target tissue site 18. Introducer 16 may, however, transition from a substantially straight shape to a curvilinear or otherwise bent shape as the need arises for a curvilinear or bent introducer 16.

In the application shown in FIG. 1, implantation of lead 14 involves the subcutaneous placement of lead 14 transversely across one or more occipital nerves 22, 24, and/or 26 that are causing patient 20 to experience pain. For treating occipital neuralgia, patient 20 may be placed in a lateral position or in a prone position during implantation of lead 14. In order to locate the specified occipital nerve causing pain, a clinician may palpate the area of pain. In addition, a screening lead may be used in some embodiments prior to implanting lead 14 to develop optimal stimulation parameters, e.g., various electrode combinations, amplitude, pulse width, and pulse rate.

In one example method of implanting lead 14 proximate to one or more occipital nerves 22, 24, and/or 26, a vertical skin incision 33 approximately two centimeters in length is made in the neck of patient 20 lateral to the midline of the spine at the level of the C1 vertebra. Typically, local anesthetic is used during the implantation procedure. Fluoroscopy may be used to identify the C1 vertebra. The length of vertical skin incision 33 may vary depending on the patient. At this location, the patient's skin and muscle are separated by a band of connective tissue referred to as fascia. Occipital nerves 22, 24, and/26 are located within the cervical musculature and overlying fascia. Thus, introducer 16 and, eventually lead 14, are inserted superficial to the fascia and muscle layer but below the skin (or scalp).

Because lead 14 is implanted just under the scalp of patient 20, care should be taken to avoid advancing introducer 16 into or through the scalp when advancing introducer 16, and in particular, distal end 16B of introducer, to target tissue site 18. In some embodiments, lead 14 may be disposed within introducer 16 as introducer is advanced through tissue to target tissue site 18, while in other embodiments, lead 14 may be introduced into introducer 16 after introducer 16 is properly position with respect to target tissue site 18. The transverse contour of the back of the neck may vary from patient to patient. For these reasons, it is advantageous that introducer 16 be configured to be manually manipulated, i.e., bendable by the clinician, to conform to the back of neck of patient 20 to avoid damage to surrounding tissue when advancing introducer 16 to target site 18.

Although occipital nerve stimulation is shown in FIG. 1, therapy system 10 is useful in other neurostimulation applications. In alternate applications of lead 14, target tissue site 18 may be a location proximate to other nerves, organs, muscles, muscle groups or other tissue sites in patient 20, which may be selected based on, for example, a therapy program selected for a particular patient 20. For example, therapy system 10 may be used to deliver neurostimulation therapy to a sacral nerve, a pudendal nerve, a perineal nerve or other areas of the nervous system, in which cases, lead 14 would be implanted and substantially fixed proximate to the respective nerve. As further examples, lead 14 may be positioned for temporary or chronic spinal cord stimulation for the treatment of pain, for peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat movement disorders and other neurological disorders. Accordingly, although patient 20 and target tissue site 18 of FIG. 1 are referenced throughout the remainder of the disclosure for purposes of illustration, introducer 16 may be adapted to facilitate implantation of an electrical stimulation lead at a variety of target tissue sites. In particular, introducer 16 may be configured so that a clinician can easily manipulate introducer 16 to conform to an anatomical structure so that introducer 16 can be advanced to a target tissue site without substantially damaging surrounding tissue.

Therapy system 10 may also include clinician programmer 32 and patient programmer 34. Clinician programmer 32 may be a handheld computing device that permits a clinician to program electrical stimulation therapy for patient 20, e.g., using input keys and a display. For example, using clinician programmer 32, the clinician may specify electrical stimulation parameters for use in delivery of neurostimulation therapy. Clinician programmer 32 supports telemetry (e.g., radio frequency (RF) telemetry) with neurostimulator 12 to download electrical stimulation parameters and, optionally, upload operational or physiological data stored by neurostimulator 12. In this manner, the clinician may periodically interrogate neurostimulator 12 to evaluate efficacy and, if necessary, modify the stimulation parameters.

Like clinician programmer 32, patient programmer 34 may be a handheld computing device. Patient programmer 34 may also include a display and input keys to allow patient 20 to interact with patient programmer 34 and neurostimulator 12. In this manner, patient programmer 34 provides patient 20 with an interface for control of neurostimulation therapy by neurostimulator 12. For example, patient 20 may use patient programmer 34 to start, stop or adjust neurostimulation therapy. In particular, patient programmer 34 may permit patient 20 to adjust stimulation parameters such as duration, amplitude, pulse width and pulse rate, within an adjustment range specified by the clinician via clinician programmer 34, or select from a library of stored stimulation therapy programs.

Neurostimulator 12, clinician programmer 32, and patient programmer 34 may communicate via cables or a wireless communication, as shown in FIG. 1. Clinician programmer 32 and patient programmer 34 may, for example, communicate via wireless communication with neurostimulator 12 using RF telemetry techniques known in the art. Clinician programmer 32 and patient programmer 34 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Figure 2:
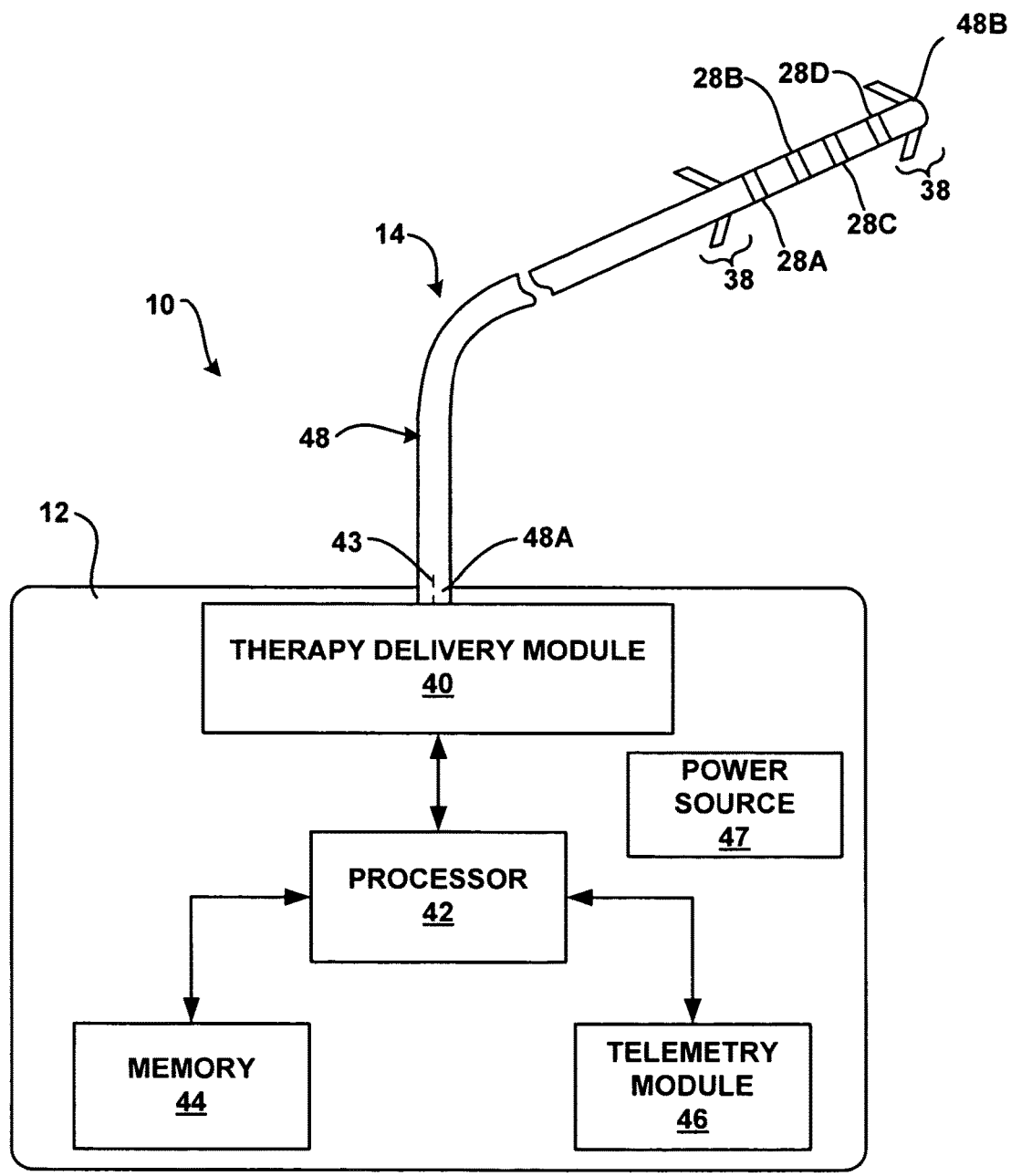
FIG. 2 is a block diagram illustrating various components of the therapy system.

FIG. 2 is a block diagram illustrating various components of neurostimulator 12 and an implantable medical lead 14. Neurostimulator 12 includes therapy delivery module 40, processor 42, memory 44, telemetry module 46, and power source 47. In some embodiments, neurostimulator 12 may also include a sensing circuit (not shown in FIG. 2). Implantable medical lead 14 includes lead body 48 extending between proximal end 48A and distal end 48B. In the embodiment of FIG. 2, lead body 48 is cylindrical. In other embodiments, however, lead body 48 may be paddle-shaped, i.e., a "paddle" lead, in which case lead body 48 would define two opposing surfaces.

Electrodes 28A, 28B, 28C, and 28D (collectively "electrodes 28") are disposed on lead body 48 adjacent to distal end 48B of lead body 48. In some embodiments, electrodes 28 may be ring electrodes. In other embodiments, electrodes 28 may be segmented or partial ring electrodes, each of which extends along an arc less than 360 degrees, e.g., approximately 90-120 degrees, around the circumference of lead body 48. The configuration, type, and number of electrodes 28 illustrated in FIG. 2 are merely exemplary.

In embodiments in which lead 14 is a paddle lead, electrodes 28 may extend along one side of lead body 48. Electrodes 28 extending around a portion of the circumference of lead body 48 or along one side of a paddle lead may be useful for providing an electrical stimulation field in a particular direction/targeting a particular tissue site. For example, in the electrical stimulation application shown in FIG. 1, electrodes 28 may be disposed along lead body 48 such that the electrodes face toward occipital nerves 22, 24, and/or 26, or otherwise away from the scalp. This may be an efficient use of stimulation because electrical stimulation of the scalp may not provide any or very minimal useful therapy to patient 20. In addition, the use of segmented or partial ring electrodes 28 may also reduce the overall power delivered to electrodes 28 by neurostimulator 12 because of the efficient delivery of stimulation to occipital nerves 22, 24, and/or 26, or other target tissue sites, by eliminating or minimizing the delivery of stimulation to unwanted or unnecessary regions within patient 20.

In embodiments in which electrodes 28 extend around a portion of the circumference of lead body 48 or along one side of a paddle lead, lead body 48 may include one or more orientation markers 43 proximate to proximal end 48A that indicate the relative location of electrodes 28. Orientation marker 43 may be a printed marking on lead body 48, an indentation in lead body 48, a fluoroscopic or radiographic marker, or another type of marker that is visible or otherwise detectable (e.g., detectable by a radiographic device) by a clinician. Orientation marker 43 may help a clinician properly orient lead 14 such that electrodes 28 face the desired direction (e.g., toward target stimulation 18) within patient 20. For example, orientation marker 43 may also extend around the same portion of the circumference of lead body 48 or along the side of the paddle lead as electrodes 28. In this way, orientation marker 43 faces the same direction as electrodes 28, thus indicating the orientation of electrodes 28 to the clinician. In one embodiment, when the clinician implants lead 14 in patient 20, orientation marker 43 may remain visible to the clinician.

Lead 14 comprises fixation elements 38 located both distal and proximal to electrodes 28. Fixation elements 38 are configured to engage with surrounding tissue when lead 14 is implanted in patient 20 in order to substantially fix lead 14, and in particular, electrodes 28, proximate to target tissue site 18. Although tine-like fixation elements 38 are shown in FIG. 2, in other embodiments, lead 14 may include any suitable fixation elements, as discussed above.

Neurostimulator 12 delivers stimulation therapy via electrodes 28 of lead 14. In particular, electrodes 28 are electrically coupled to a therapy delivery module 40 of neurostimulator 12 via conductors within lead body 48. In one embodiment, an implantable signal generator or other stimulation circuitry within therapy delivery module 40 delivers electrical signals, e.g., pulses or substantially continuous-time signals, such as sinusoidal signals, to target tissue site 18 via at least some of electrodes 28 under the control of a processor 42. The implantable signal generator may be coupled to power source 47. Power source 47 may take the form of a small, rechargeable or non-rechargeable battery, or an inductive power interface that transcutaneously receives inductively coupled energy. In the case of a rechargeable battery, power source 47 similarly may include an inductive power interface for transcutaneous transfer of recharge power.

The stimulation energy generated by therapy delivery module 40 may be formulated as neurostimulation energy, e.g., for treatment of any of a variety of neurological disorders, or disorders influenced by patient neurological response. The signals may be delivered from therapy delivery module 40 to electrodes 28 via a switch matrix and conductors carried by lead 14 and electrically coupled to respective electrodes 28.

Processor 42 may include a microprocessor, a controller, a DSP, an ASIC, an FPGA, discrete logic circuitry, or the like. Processor 42 controls the implantable signal generator within therapy delivery module 40 to deliver neurostimulation therapy according to selected stimulation parameters.

Specifically, processor 42 controls therapy delivery module 40 to deliver electrical signals with selected amplitudes, pulse widths, and rates specified by the programs. In addition, processor 42 may also control therapy delivery module 40 to deliver the neurostimulation signals via selected subsets of electrodes 28 with selected polarities. For example, electrodes 28 may be combined in various bipolar or multipolar combinations to deliver stimulation energy to selected sites, such as nerve sites adjacent the spinal column, pelvic floor nerve sites, or cranial nerve sites.

Processor 42 may also control therapy delivery module 40 to deliver each stimulation signal according to a different program, thereby interleaving programs to simultaneously treat different symptoms or provide a combined therapeutic effect.

Memory 44 of neurostimulator 12 may include any volatile or non-volatile media, such as a RAM, ROM, NVRAM, EEPROM, flash memory, and the like. In some embodiments, memory 44 of neurostimulator 12 may store multiple sets of stimulation parameters that are available to be selected by patient 20 via patient programmer 34 (FIG. 1) or a clinician via clinician programmer 32 (FIG. 1) for delivery of neurostimulation therapy. For example, memory 44 may store stimulation parameters transmitted by clinician programmer 32 (FIG. 1). Memory 44 also stores program instructions that, when executed by processor 42, cause neurostimulator 12 to deliver neurostimulation therapy. Accordingly, computer-readable media storing instructions may be provided to cause processor 42 to provide functionality as described herein.

In particular, processor 42 controls telemetry module 46 to exchange information with an external programmer, such as clinician programmer 32 and/or patient programmer 34 (FIG. 1), by wireless telemetry. In addition, in some embodiments, telemetry module 46 supports wireless communication with one or more wireless sensors that sense physiological signals and transmit the signals to neurostimulator 12.

Introducer 16 may include one or more components. FIGS. 3A and 3B are schematic diagrams illustrating an embodiment of introducer 16 in greater detail. As shown in FIGS. 3A and 3B, introducer 16 includes dilator 52 and sheath 50 configured to interchangeably receive dilator 52 and lead 14. In particular, FIG. 3A illustrates dilator 52 partially inserted into sheath 50 and FIG. 3B illustrates dilator 52 fully inserted into sheath 50. As previously described, introducer 16 is configured to flex more easily in at least one direction than at least one other direction and may be used to facilitate implantation of medical lead 14 within patient 20 (FIG. 1), e.g., transversely across one or more of occipital nerves 22, 24, and 26 (FIG. 1) superficial to fascia and muscle tissue but below the skin, i.e., scalp. In particular, introducer 16 is useful for conforming to the transverse contour of the neck or head of patient 20. As a result, the clinician may accurately position lead 14 to delivery therapy to target tissue site 18 while minimizing the possibility of substantially damaging surrounding tissue.

Figure 4:
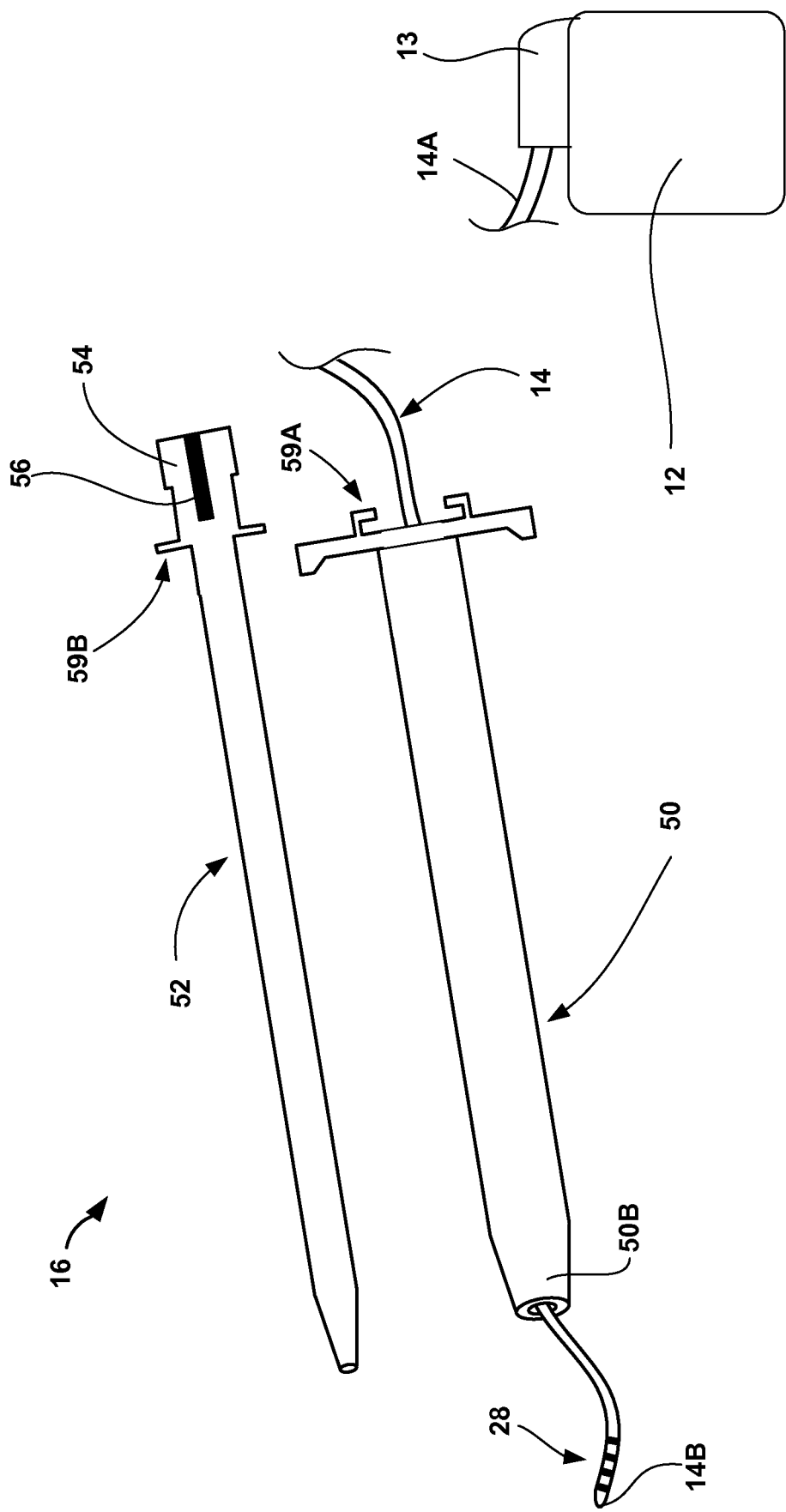
FIG. 4 is a schematic diagram illustrating a therapy element inserted in the introducer.

In the illustrated example, sheath 50 includes an elongated body 51 that defines lumen 58 sized to interchangeably receiving dilator 52 and medical lead 14. Lumen 58 may have a circular, oval, square, or rectangular cross-sectional shape (where the cross-section is taken in an axial direction), although any shape is possible, and may be sized to accommodate dilator 52 and any medical lead. Medical lead 14 may be inserted through lumen 58 of sheath 50, as shown in FIG. 4, when dilator 52 is withdrawn from sheath 50, such as after introducer 16 has been properly positioned with respect to target tissue site 18. In one embodiment, sheath 50 may be withdrawn to implant medical lead 14 at target tissue site 18, while in another embodiment, lead 14 may be advanced through sheath 50 to deploy electrodes 28 into tissue proximate to target tissue site 18. Sheath 50 may also help prevent premature engagement of fixation elements 38 with surrounding tissue by separating fixation elements 38 from surrounding tissue until lead 14 is properly positioned proximate to target tissue site 18.

Sheath 50 may also include visible markers 49A-E that are detectable by imaging techniques, such as fluoroscopic imaging or x-ray imaging. In other embodiments, markers 49A-E may be visible without the aid of imaging techniques. For example, markers 49A-E may be printed markings (e.g., lines, text or graphical symbols) on sheath 50, an indentation in sheath 50 or another type of marker that is visible or otherwise detectable (e.g., detectable by a radiographic device) by the clinician. Markers 49A-E may be helpful for maneuvering sheath 50 relative to target tissue site 18 when inserting sheath 50 within patient 20. For example, marker 49A near proximal end 50A of sheath 50 may remain visible to the clinician as clinician guides sheath 50 and dilator 52 into patient 20, thus indicating the approximate depth of introducer 16 and the relative location of distal end 50B of sheath 50. Markers 49A-E may also be useful for indicating a relative depth of sheath 50 within patient 20. For example, the clinician may observe markers 49A-E to determine whether sheath 50 has inadvertently been withdrawn from patient 20 or to determine the approximate depth of distal end 50B of sheath 50 within patient 20. The clinician may, for example, locate a marker 49A-E with respect to skin of the patient 20.

Sheath 50 may be fabricated with a "soft" plastic, biocompatible elastomeric material, a biocompatible stainless steel or other soft biocompatible metals, a biocompatible plastic with embedded bands or wires, thermoformed biocompatible plastics, high density polyethylene, biocompatible malleable materials, or other flexible biocompatible materials that may retain a curved shape. Thus, in one embodiment, sheath 50 is flexible over its entire length, thereby allowing it to receive dilator 52 regardless of the shape of dilator 52. As a result, as introducer 16 is advanced toward target site 18 in a series of steps, dilator 52 can be inserted and withdrawn from sheath 50 while sheath 50 remains implanted within patient 20. When dilator 52 is withdrawn from sheath 50 to be manipulated into a desired shape, sheath 50 remains inserted in patient 20 and acts as a "place holder." That is, sheath 50 prevents any blockage from forming along the insertion path initially defined by dilator 52 and sheath 50 when dilator 52 is removed from sheath 50 and from patient 20. After dilator 52 is manipulated into a desired shape, dilator 52 is re-inserted into sheath 50 and further advanced toward target site 18. In this manner, sheath 50 prevents unnecessary damage to surrounding tissue when dilator 52 is repeatedly withdrawn and inserted.

Alternatively, sheath 50 may include one or more flexible portions that are configured to preferentially flex in one direction over at least one other direction. That is, instead of being flexible to conform to a contour of dilator 52, sheath 50 may be manipulated to conform to the back of the neck or other anatomical structure of patient 20 and dilator 52 may be configured to take the shape of sheath 50. In this case, the clinician may advance sheath 50 with dilator 52 inserted therein toward target site 18 in a series of steps by partially inserting sheath 50, withdrawing sheath 50 to manipulate sheath 50 into a desired shape, and re-inserting sheath 50 into patient 20 to further advance sheath 50 towards target site 18. Thus, in some embodiments, sheath 50 may be used to steer the direction of an insertion path through tissue for a therapy element. In some embodiments, both sheath 50 and dilator 52 may have flexible portions that are configured to preferentially flex in one direction over at least one other direction. In such an embodiment, sheath 50 and dilator 52 may or may not preferentially flex in the same direction.

Dilator 52 may be similar to a Tuohy needle or other instrument used to dissect tissue to facilitate implanting a medical lead within tissue of a patient. In some embodiments, to facilitate implantation of lead 14, for example transverse to one or more of occipital nerves 22, 24, and 26, dilator 52 may have a length of approximately 2 centimeters (cm) to approximately 40 cm. For example, in one embodiment, dilator 52 may have a length of approximately 5 cm to approximately 15 cm, or in another embodiment, approximately 9 cm to approximately 20 cm. In some embodiments, dilator 52 may have a diameter of approximately 1 millimeter (mm) to approximately 10 mm. For example, in one embodiment, dilator 52 may have a diameter of approximately 1 mm to approximately 5 mm. The cross section of dilator 52 may be circular, oval, square, or rectangular shape, although any shape is possible.

Dilator 52 has sufficient rigidity to hold its shape while being advanced through tissue while, at the same time, including at least a portion that is configured to bend more easily in at least one direction than at least one other direction. In this way, the dilator can be manipulated to conform to an anatomical structure, such as the transverse contour of the back of the neck, an area above or below the eye, or other anatomical structure having an irregular shape or a shape that varies between patients. To aid in tissue dissection, the distal end of dilator 52 may be tapered to an edge or pointed and extend beyond distal end 50B of sheath 50, as shown in FIGS. 3A and 3B.

Dilator 52 may also include visible markers similar to visible markers 49A-E of sheath 50. The markers on dilator 52 may be helpful for determining the relative locations of dilator 52 and sheath 50, as well as the relative location of distal end 52B of dilator 52 within patient 20.

In one example, dilator 52 may be predisposed to be more flexible in one direction than at least one other direction along its entire length (measured from proximal end 52A to distal end 52B). In another example, a portion of dilator 52 may be predisposed to be more flexible in one direction than at least one other direction. The flexible portion may be located at or near the distal end 52B of dilator 52, at or near proximal end 52A of dilator 52, or medially located between distal end 52B and proximal end 52A. The flexible portion may be substantially longer than the remaining portion of dilator 52, approximately half the length of dilator 52, or substantially shorter than the remaining, inflexible length of dilator 52.

Figure 9:
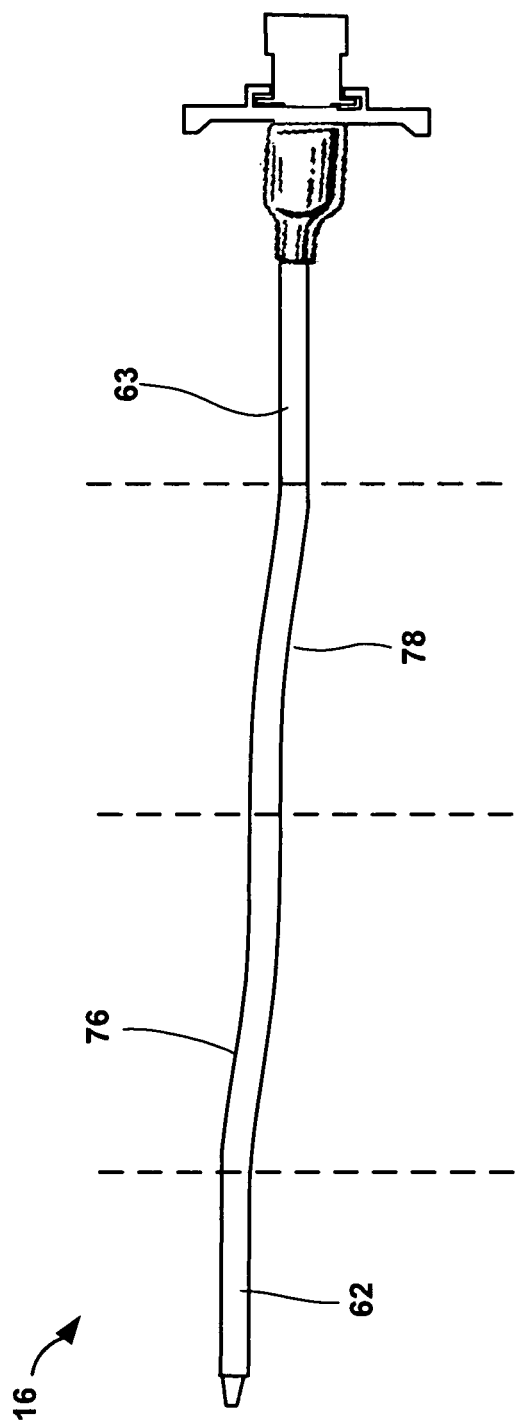

The length of the flexible portion may be chosen based on the implant site. Dilator 52 may also have more than one flexible portion. In this case, each portion may be flexible in the same direction or, for example, may be flexible in opposite directions to form an S-shape (e.g., as shown in FIG. 9). The portions may be adjacent to each other or may be separated by a substantially rigid portion. In this manner a portion or entire length of dilator 52 may be manipulated into an arc, an S-shape, or other curvilinear shape that bends in one or more directions. FIGS. 5A-9 illustrate a dilator manipulated into various exemplary shapes. The flexible portion of dilator 52 may allow a clinician to more accurately position dilator 52 within patient 20 by allowing the clinician to shape dilator 52 as the need arises. The ability of dilator 52 to change shape based on the specific patient or implant site may help reduce the likelihood of trauma to surrounding tissue, particularly with respect to an anatomical structure having an irregular shape or a shape that varies between patients, such as the back of the neck. Dilator 52 may also be configured to resist being manipulated into an unwanted shape.

Hub 54 is located at the proximal end of dilator 52 and provides a handle with which the clinician may hold dilator 52. Hub 54 may be ergonomically designed to enable the clinician to easily and firmly grip dilator 52 when advancing introducer 16, i.e., dilator inserted into sheath 50, through tissue of patient 20. Hub 54 may also be configured to connect to a syringe for infusion of a local anesthetic.

Dilator 52 and sheath 50 also include interlocking members 59B and 59A, respectively, which interlock with each other when dilator 52 is fully inserted into sheath 50. To insert dilator 52 into sheath 50, dilator 52 is rotated (as indicated by arrow 55) about a longitudinal axis of sheath 50 to allow interlocking member 59B to pass through the opening formed by interlocking member 59A. Dilator 52 can then be inserted into sheath 50 until interlocking member 59B abuts against the opening 58A to lumen 58 of sheath 50. Dilator 52 can then be rotated as shown in FIG. 3B so that interlocking members 59A and 59B are interlocked with each such that a clinician can control movement of the entire introducer assembly 16 by grasping hub 54. This also enables the clinician to withdraw both sheath 50 and dilator 52 after medical lead 14 has been positioned within patient 20. When fully inserted, distal end 52B of dilator 52 may extend through distal end 50B of sheath 50, as shown in FIG. 3B, so that distal end 52B of dilator 52 can be used to dissect tissue when inserted into patient 20.

One or more orientation markers 56 may be located on hub 54 to indicate the direction in which dilator 52 bends more easily. Orientation marker 56 may, for example, be a printed marking on hub 54, an indentation in hub 54, or other type of visible marker, tactile marker, or marker that is otherwise detectable (e.g., by fluoroscopy or radiography) by the clinician. In other examples, orientation marker 56 may be located on dilator 52. In such examples, orientation marker may be a radiographic marker detectable by a radiographic device or other marker detectable within a patient. In any case, orientation marker 56 may help a clinician properly orient dilator 52 such that the shape of dilator 52 is aligned with the intended path of advancement. That is, the clinician may use orientation marker 54 as a reference when advancing dilator 52 through tissue to ensure that dilator 52 is oriented in the proper direction to avoid possibly extending dilator 52 into or through the skin (scalp) of patient 20 or otherwise damage surrounding tissue. For example, because dilator 52 may be manipulated to form an arc or another curvilinear shape to conform to the back of the neck of patient 20, dilator 52 should be oriented such that dilator 52 curves anterior into patient 20. In this example, orientation marker 56 may face an opposite direction of the curve in dilator 52 so that orientation marker 56 remains visible to the clinician when advancing introducer 16 into patient 20.

Generally, a clinician may advance introducer 16, i.e., dilator 52 and sheath 50, to target tissue site 18 in a series of steps. The steps may include partially advancing introducer 16, withdrawing dilator 52 from sheath 50, manipulating dilator 52 to conform to the back of the neck of patient 20, and re-inserting dilator 52 into sheath 50 (which remains within an insertion path defined by introducer 16) to further advance introducer 16, i.e., dilator 52 and sheath 50, to target tissue site 18. These steps may be repeated as necessary until introducer 16 is advanced to target site 18 and distal end 52B of dilator 52 or distal end 50B of sheath 50 is properly positioned proximate to target tissue site 18. Proper positioning may be, for example, the positioning desired to implant electrodes 28 of lead 14 proximate to target tissue site 18. The clinician may use fluoroscopic guidance or another suitable technique to identify occipital nerves 22, 24, and 26 and determine how to manipulate introducer 16 to conform to the back of the neck of patient 20. In other words, the clinician may use fluoroscopy aid in determining the length and angle of the portion to manipulate.

When introducer 16 is advanced to target site 18, dilator 52 is removed from sheath 50. Lead 14 may then be advanced through sheath 50 and positioned to allow stimulation of the lesser occipital nerve 22, greater occipital nerve 24, third occipital nerve 26, trigeminal nerve and/or other peripheral nerves proximate to an occipital nerve or a trigeminal nerve. The position of lead 14 may be verified via fluoroscopy. In addition, the clinician may confirm that the electrodes 28 proximate to distal end 14A of lead 14 are properly placed with respect to the particular occipital nerve. For example, the clinician may provide electrical signals to the electrodes and patient 20 may provide feedback relating to the paresthesia coverage or side effects resulting from the electrode placement. Upon placement of lead 14, sheath 50 of introducer 16 may be removed either before or after confirming the placement of electrodes 28. However, if sheath 50 remains in patient 20 until electrodes 28 are placed in operative relation to target tissue site 18, the clinician may utilize sheath 50 to easily reposition electrodes 28 of lead 14 with respect to target tissue site 18 because sheath 50 helps provide a relatively resistance-free insertion path from the scalp or epidermis of patient 20 to target tissue site 18.

FIG. 4 is a schematic diagram illustrating medical lead 14 inserted into introducer 16. More specifically, FIG. 4 shows dilator 52 removed from sheath 50 to allow medical lead 14 to be inserted through sheath 50. Although distal end 14B of medical lead 14 is shown extending past distal end 50B of sheath 50, in some embodiments, when positioning lead 14 within patient 20, lead 14 may be inserted into sheath 50 such that distal end 14B is substantially aligned with distal end 50B of sheath 50. In other words, distal end 14B of lead 14 may not extend through sheath 50. When medical lead 14 is inserted into sheath 50, the clinician may position lead 14 such that electrodes 28 are centered over the targeted occipital nerves or other target tissue site 18. After medical lead 14 is positioned, the clinician may remove sheath 50 from the patient, for example, by grasping interlocking mechanism 59A or other structure protruding from sheath 50, thereby leaving lead 14 implanted within patient 20.

As previously described, lead 14 may include one or more fixation elements 38 (shown in FIG. 2) to help substantially fix lead 14 to target tissue site 18. The fixation elements may be any suitable actively or passively deployed fixation elements that help prevent migration of lead 14. In the embodiment shown in FIG. 4, sheath 50 is sized to receive lead 14 and fixation elements 38, which typically protrude from lead 14.

Although introducer 16 may be manipulated to bend in the predisposed directions, introducer 16 is illustrated in FIGS. 3A-4 as being in an non-flexed state, in which introducer 16 is substantially straight along its entire length and the entire length of introducer 16 is substantially axially aligned with the proximal and distal ends 16A and 16B of introducer 16. That is, dilator 52 and sheath 50 are illustrated as being substantially straight along their respective lengths (measured from the respective proximal end 52A, 50A to the respective distal end 52B, 50B). In some embodiments, introducer 16 may have a curved shape in its non-flexed state. Prior to insertion into patient 20, dilator 52 and sheath 50 may be substantially straight, as shown in FIGS. 3A-4, which may allow dilator 52 and sheath 50 to be initially inserted into patient 20 through incision 33 more easily. Upon insertion into patient 20 or prior to insertion into patient 20, introducer 16 may be manipulated into various shapes.

Figure 5A:
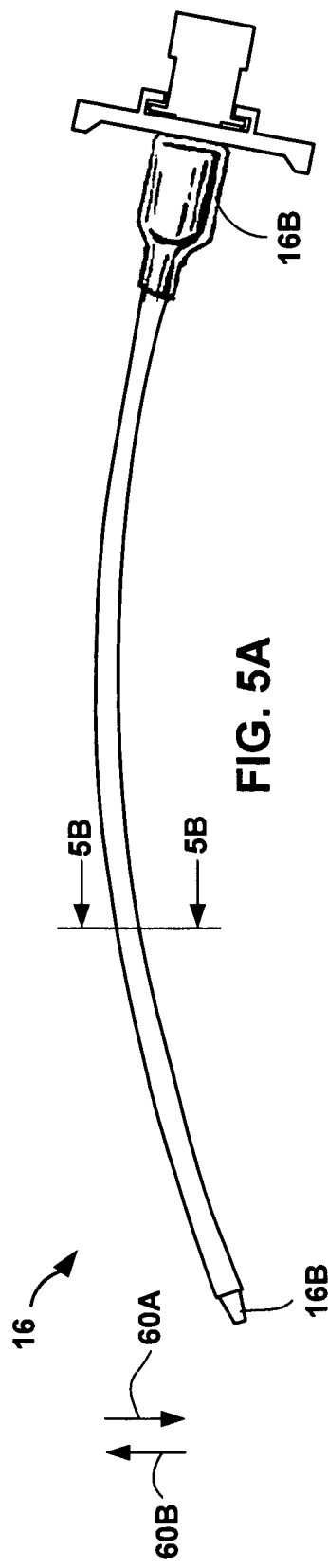

FIGS. 5A-9 are schematic diagrams illustrating configurations and shapes for introducer 16. In particular, FIG. 5A illustrates introducer 16 that is flexed into a curvilinear shape that may conform to a substantially transverse contour to the back of the neck of patient 20. While introducer 16 may have a maximum curvature, introducer 16 does not necessarily have a predetermined curvature. That is, a clinician may manipulate introducer 16 to achieve a desired curvature for a particular patient to the extent allowed by introducer 16. In this way, a single introducer 16 may exhibit a different curvature for different applications or for different patients. Once the flexible portions of introducer 16 are flexed into a shape, introducer 16 typically remains in the shape until the clinician manipulates introducer 16 again.

In FIG. 5A, introducer 16 is curved substantially along its entire length, from proximal end 16A to distal end 16B, to form a curvilinear shape. Although introducer 16 is shown in FIG. 5A as having a substantially constant radius of curvature, the radius of curvature may vary along its length, i.e., the radius of curvature may be greater near proximal end 16A and lesser at the distal end 16B, or vice versa. Alternatively, the radius of curvature may be lesser at the proximal and distal ends 16A and 16B, respectively, and greater along a portion medially located between the proximal and distal ends 16A and 16B, respectively.

In any case, the ability to manipulate introducer 16 to have a curved shape along substantially its entire length may enable introducer 16 to better conform to an anatomical structure, such as the back of the neck or head, than would be possible using another introducer that does not bend, or has a predetermined curve. Specifically, being able to manipulate introducer 16 during implantation may be advantageous when inserting introducer proximate to anatomical structures having an irregular shape or a shape that varies from patient to patient.

Figure 5B:
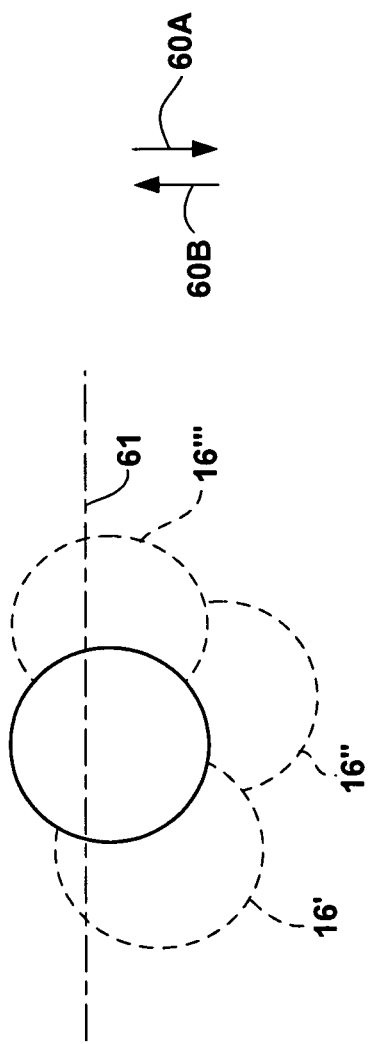

In the embodiment of introducer 16 shown in FIG. 5A, introducer 16 is configured to flex in one direction, indicated by arrow 60A, while configured to substantially resist flexing in the opposite direction, indicated by arrow 60B. FIG. 5B is a schematic cross-sectional view of introducer 16 taken along line 5B-5B in FIG. 5A, and illustrates axis 61. Introducer 16 may flex in direction 60A, along axis 61, or any direction generally in the direction 60A and along axis 61, as illustrated by introducers 16', 16", and 16''' (shown in phantom lines). Resisting manipulation in certain directions (e.g., direction 60B) may prevent damage to surrounding tissue while advancing introducer 16 through tissue. For example, direction 60B may face toward the skin of patient 20, in which case it may be desirable for introducer 16 to resist flexing in direction 60B toward the skin of patient. Thus, in the embodiment shown in FIGS. 5A and 5B, it is unlikely that introducer 16 will bend in an undesirable direction due to various forces it may experience as introducer 16 is advanced through tissue, because introducer 16 is configured to resists manipulation in certain directions (e.g., direction 60B).

Figure 6:
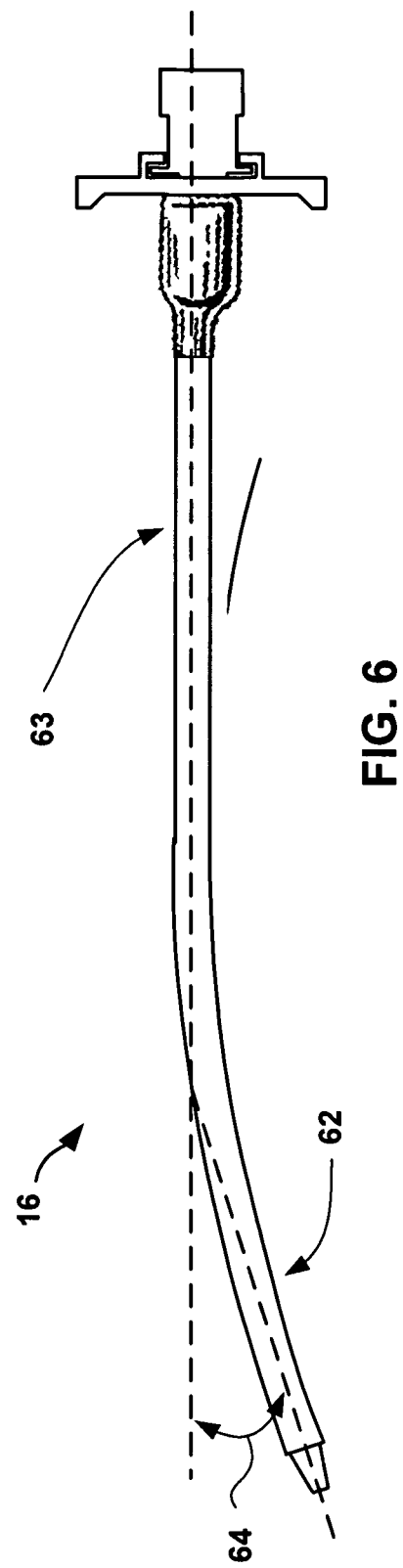

FIG. 6 illustrates introducer 16 as including a curved distal portion 62 and a substantially straight proximal portion 63. Curved distal portion 62 may form an angle within a range of approximately 10 degrees to approximately 30 degrees (measured in the direction indicated by arrow 64) with respect a substantially longitudinal axis of introducer 16 in a non-flexed state. In some embodiments, distal portion 62 may be substantially straight and proximal portion 63 may be curved. In other embodiments, the proximal and distal portions 63, 62 of introducer 16 may be substantially straight and a portion medially located between proximal and distal portions 63, 62 may be curved.

In the illustrated example, the curved portion, i.e., distal portion 62, is approximately half the length of proximal portion 63, but curved portion distal portion 62 may be substantially longer than proximal portion 63 or substantially shorter than proximal portion 63.

In FIG. 7, distal portion 62 and proximal portion 63 are substantially straight and portion 66 medially located between distal and proximal portions 62, 63 is curved. In particular, medially located portion 66 is curved substantially along its entire length. Similar to the shape illustrated in FIG. 5A, the radius of curvature of medially located portion 66 may be substantially constant or may vary along the length of portion 66. In one embodiment, distal, proximal, and medial portions 62, 63, and 66, respectively, have substantially similar lengths.

FIG. 8 illustrates introducer 16 with more than one portion that may bend more easily in at least one direction than at least one other direction. Specifically, introducer 16 includes a first flexible portion 70 and a second flexible portion 72 in FIG. 8. First flexible portion 70 is located at or near distal portion 62 and second flexible portion 72 is located at or near proximal portion 63. First and second flexible portions 70, 72 are separated by a substantially straight portion of medially located portion 66. In some embodiments, medially located portion 66 may not be more easily flexible in any direction, i.e., may be rigid to resist bending in any direction, while in other embodiments, medical portion 66 may be flexed in a particular direction, which may or may not be the same as the directions in which portions 70 and 72 flex. Both first and second flexible portions 70, 72 are configured to bend more easily in the same direction and not in other directions. This shape may conform well to anatomical structures having curved edges and a substantially straight middle portion.

In some embodiments, at least two portions 62, 63, 66, 70, and 72 may have the same degree of flexibility. In other embodiments, at least two portions 62, 63, 66, 70, and 72 have different degrees of flexibility, in which case the two portions 62, 63, 66, 70, and/or 72 may have substantially different curvatures when bent (or flexed).

FIG. 9 illustrates introducer 16 with flexible portions that are configured to bend more easily in different directions. That is, flexible portion 76 is configured to bend more easily in one direction and not other directions and flexible portion 78 is configured to bend more easily in another direction and not other directions. As shown in FIG. 9, flexible portions 76, 78 are adjacent to each other and configured to bend more easily in opposite directions. As a result, introducer 16 can be manipulated into an S-shape, as shown in FIG. 9.

In some embodiments, at least the flexible portion of dilator 52 may be formed in part of a metal alloy, polymer, or another material that exhibits some elasticity, while still maintaining sufficient rigidity to define or otherwise maintain an insertion path through tissue of patient 20. FIGS. 10A, 10B, 11, 12A and 12B illustrate various configurations for introducer 16. More specifically, FIGS. 10A-12B illustrate various implementations for dilator 52 that enable dilator 52 to bend more easily in at least one direction than at least one other direction. Although this disclosure generally describes an introducer that is configured to bend more easily in at least one direction than at least one other direction, in the embodiments described in FIGS. 10A-12B, it is the dilator component of the introducer that is manipulated by a clinician to conform to an anatomical structure of a patient, such as the back of the neck of patient 20. Accordingly, FIGS. 10A-12 each illustrate a different implementation for dilator 52 that enables dilator 52 to be configured as described in this disclosure. However, any suitable technique for forming dilator 52 or introducer 16 that includes one or more portions that preferentially flex in at least one direction over at least one other direction may be used.

Figures 10A, 10B:
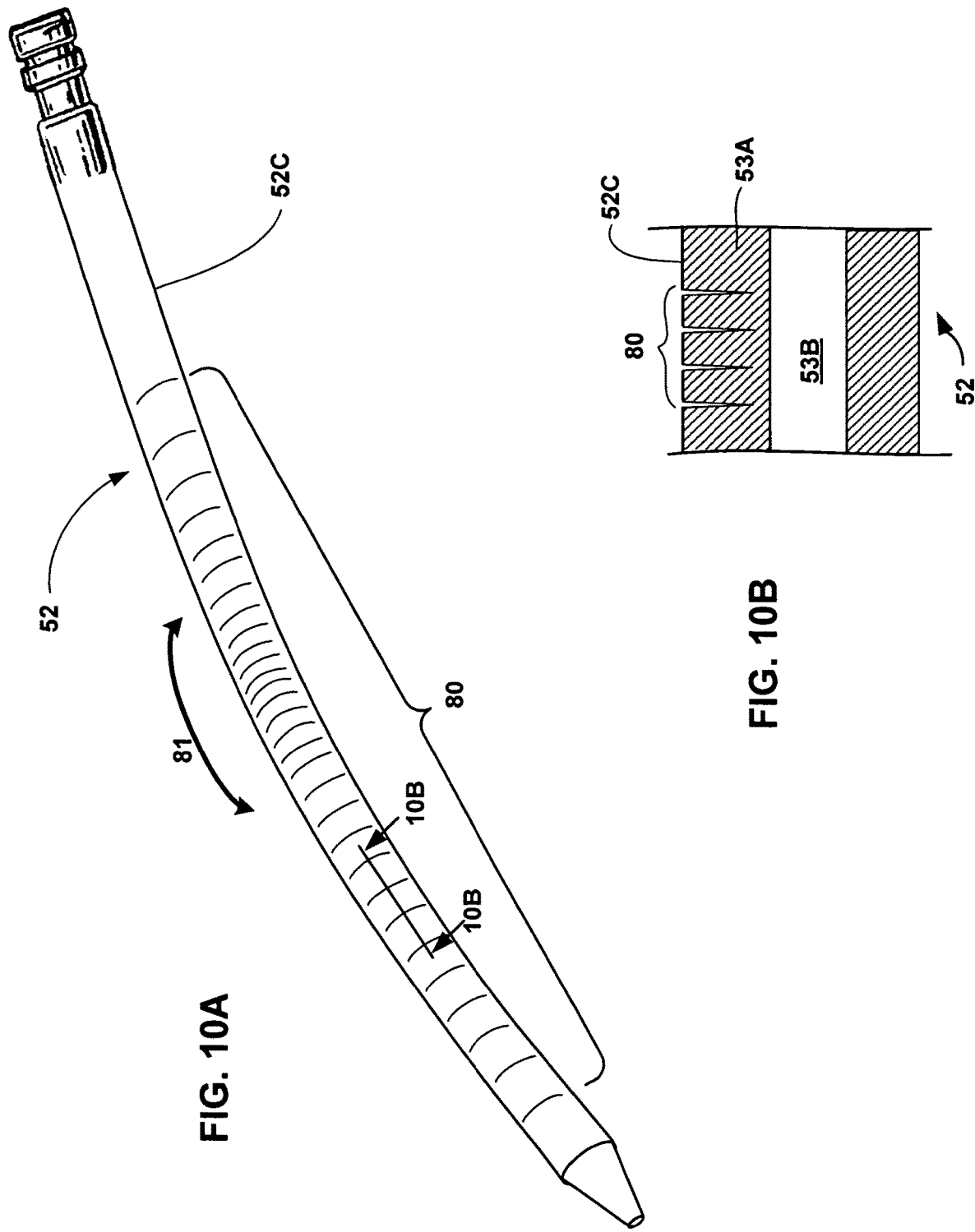

In particular, FIG. 10A is a schematic diagram illustrating dilator 52 having a plurality of grooves 80, such as striations, apertures or channels, that help dilator 52 preferentially flex toward the surface of dilator 52 defining grooves 80, as indicated by arrows 81. Although FIG. 10 shows grooves 80 formed in dilator 52, other features may be formed in dilator 52 to help dilator 52 preferentially flex towards the surface in which the features are formed. Grooves 80 generally includes features that remove material from an exterior surface of dilator 52 or otherwise provide a portion that exhibits a lesser stiffness than other parts of dilator 52 may be used. Grooves 80 may or may not be symmetrical, and grooves 80 may only include a single groove that spans across a flexible portion of dilator 50. In another example, the exterior surface may be corrugated to help dilator 52 preferentially flex along the corrugated surface. In one embodiment, grooves 80 extend along the entire length of the flexible portion of dilator 52. FIG. 10B is a schematic cross-sectional view of dilator 52 and grooves 80 and illustrates how grooves 80 extend partially through an outer surface layer 53A of dilator 52 and do not penetrate through to dilator lumen 53B. In some embodiments, dilator 52 may be solid and may not define lumen 53B. In the embodiment shown in FIGS. 10A and 10B, grooves 80 are substantially perpendicular to a longitudinal axis (extending generally from proximal end 52A to distal end 52B) of dilator 52.

In the illustrated example, grooves 80 extend along substantially the entire length of dilator 52. However, in other examples, grooves 80 may extend along approximately half of the length of dilator 52 or approximately less than half of the length of dilator 52. Grooves 80 may extend at least partially around a circumference of the exterior surface 52C of dilator 52. For example, grooves 80 may extend approximately half way around the circumference of dilator 52 or approximately less than half way around the circumference of dilator 52. In some embodiments, grooves 80 may be positioned on an inner surface of dilator 52.

Grooves 80 essentially perforate the outer surface layer 52C of dilator 52, weakening the rigidity of dilator 52 along the surface in which grooves 80 are formed. If grooves 80 extend substantially around the complete circumference, dilator 52 may flex in all directions and may not be configured to resist flexing in a particular direction. However, in some embodiments, grooves 80 may extend around the entire outer perimeter of dilator 52, with deeper or wider grooves along one side of dilator 52 such that dilator 52 may preferentially flex along or toward the surface including the deeper or wider grooves.

In addition, the spacing of grooves 80 relative to one another may determine the extent to which dilator 52 can be flexed in the desired direction. That is, closely spaced grooves 80 enable dilator 52 to bend more easily along the perforated surface as well as bend to a greater degree. As shown in FIG. 10A, in one embodiment, some of grooves 80 may be closer to each other than other grooves 80 (i.e., grooves may be unevenly spaced with respect to each other). In other embodiments, grooves 80 may be evenly spaced along dilator 52. Grooves 80 may also help outer surface 52C of dilator 52 remain substantially smooth when dilator 52 is flexed, thereby preventing outer surface 52C of dilator 52 from "wrinkling" when dilator 52 bends along the perforated surface.

Figure 11:
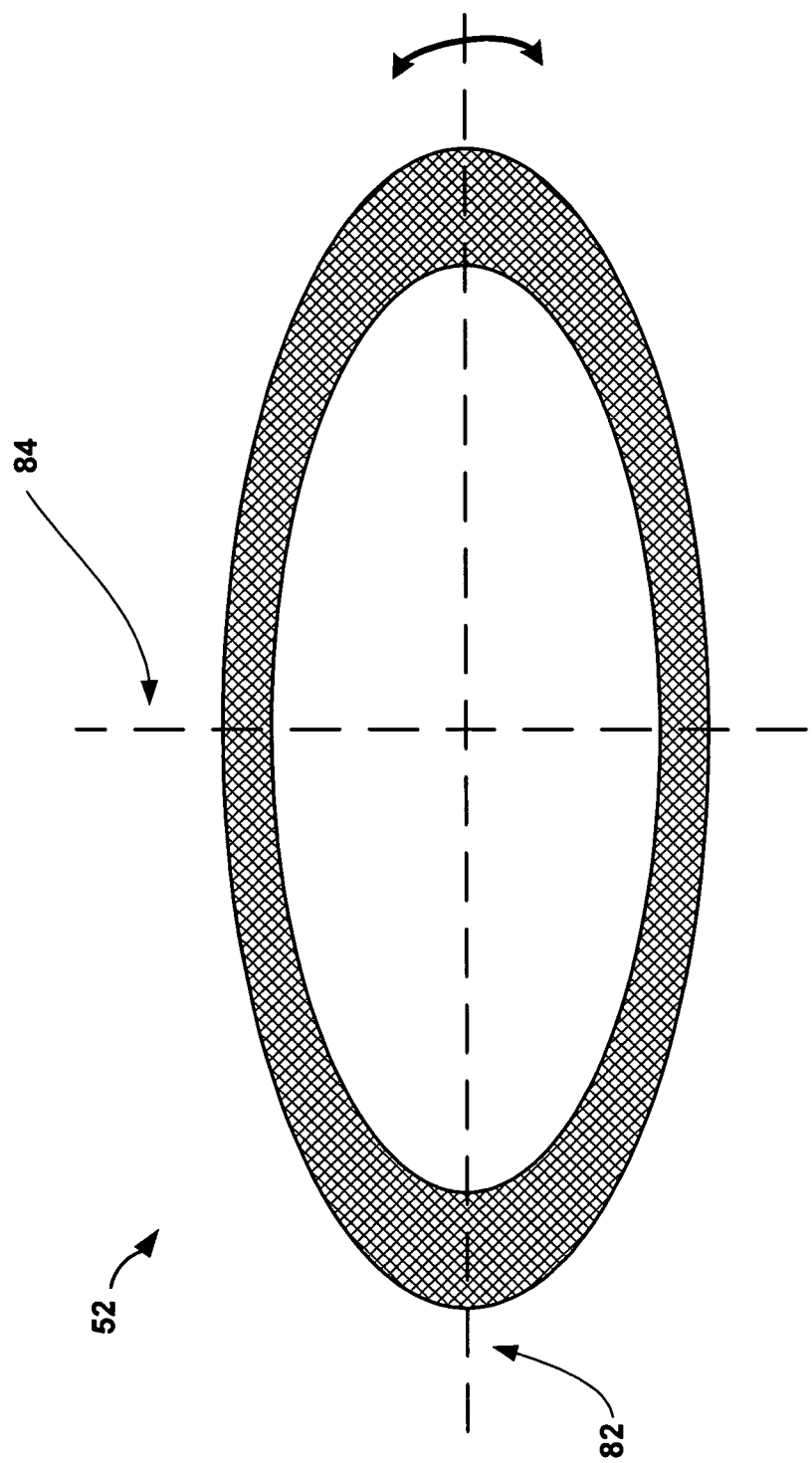

FIG. 11 illustrates a cross-sectional view of dilator 52. In the illustrated example of FIG. 11, the cross-section of dilator 52 has an oval (or elliptical) shape. The oval shape of the cross section is characterized by major axis 82 and minor axis 84, which is perpendicular to major axis 82. The oval cross-section of dilator 52 predisposes dilator 52 to bend more easily about major axis 82 than minor axis 84. An elongated body including a cross-sectional shape having a greater dimension along a one axis (e.g., a major axis) over another axis (e.g., a minor axis) is likely to exhibit preferential bending along one axis over another compared to an elongated body having a cross-sectional shape that is substantially symmetrical in all directions. With respect to elongated dilators 52 having a flexible portion that has an elliptical cross-section, a dilator having an elliptical cross-section with a greater eccentricity is more likely to exhibit preferential bending along one axis over another compared to a dilator having an elliptical cross-section having a lesser eccentricity.

Dilator 52 is not limited to an oval shaped cross-section. Rather, the cross section of dilator 52 may take any shape that predisposes dilator 52 to bend more easily in at least one direction than at least one other direction.

Figure 12A:
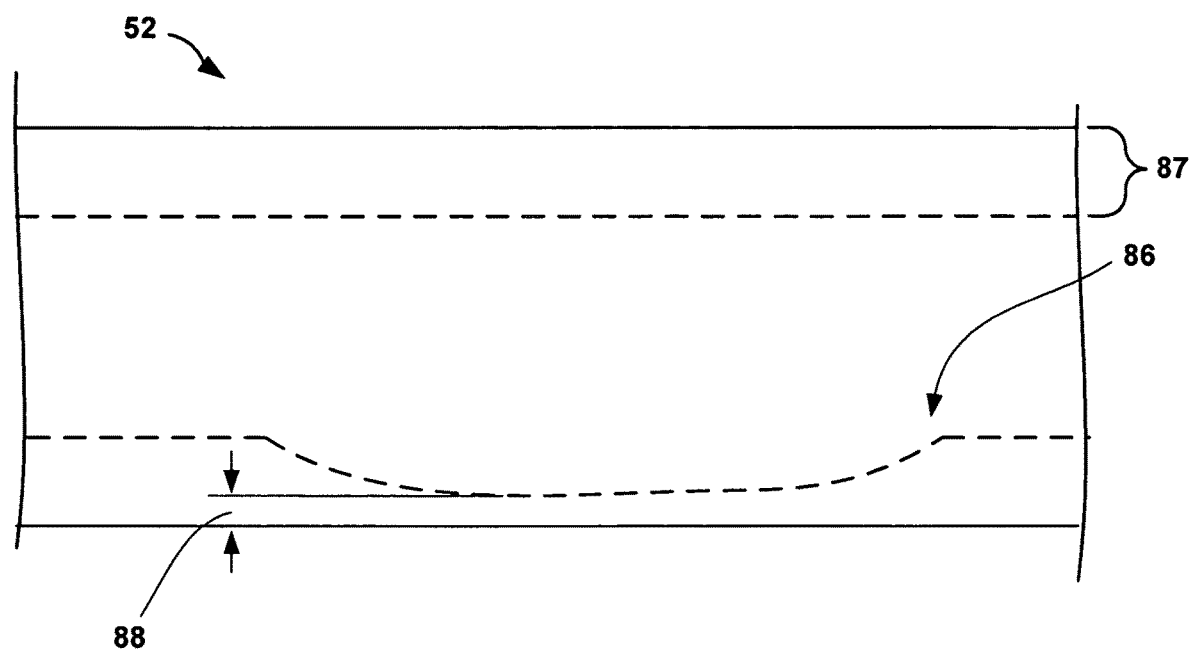
Figure 12B:
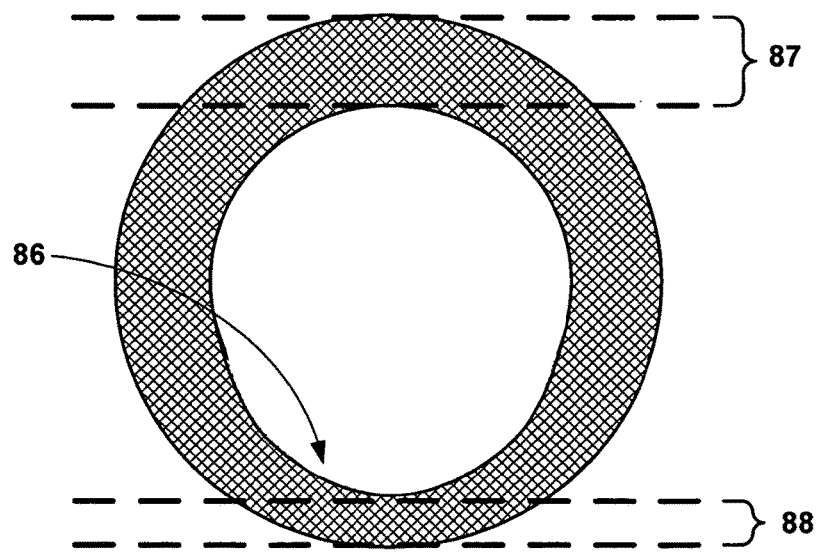

FIGS. 12A and 12B illustrate dilator 52, in which at least a portion of an inner wall 86 of dilator 52 has a reduced thickness. In particular, FIG. 12A illustrates a cross-section taken along the axial direction of dilator 52 while FIG. 12B illustrates a cross-section taken perpendicular to the axial direction of dilator 52. The reduced thickness 88 of inner wall 86 decreases the rigidity of dilator 52 along inner wall 86. As a result, dilator 52 may be predisposed to bend more easily along the surface of inner wall 86 having reduced thickness 88.

As shown in FIG. 12B, reduced thickness 88 of inner wall 86 may extend partially around the circumference. For example, reduced thickness 88 may extend approximately half way around inner wall 86 or approximately less than half way around inner wall 86. It In addition, reduced thickness 88 may extend at least partially along the length of dilator 52, as shown in FIG. 12A. In the example of FIG. 12A, the portion of dilator 52 having reduced thickness 88 may bend more easily in at least one direction than at least one other direction while the portion of dilator 52 having a greater thickness 87 than thickness 88 may provide substantial rigidity to resist bending in any direction. In other examples, however, reduced thickness 88 may extend along substantially the entire length of dilator 52 to allow dilator 52 to bend more easily along substantially its entire length.

In embodiments in which sheath 50 exhibits preferential flexibility, the flexible portions of sheath 50 may also include grooves 80, a cross-sectional shape having a major and minor axis or varying thickness (FIGS. 12A-B).

Figure 13:
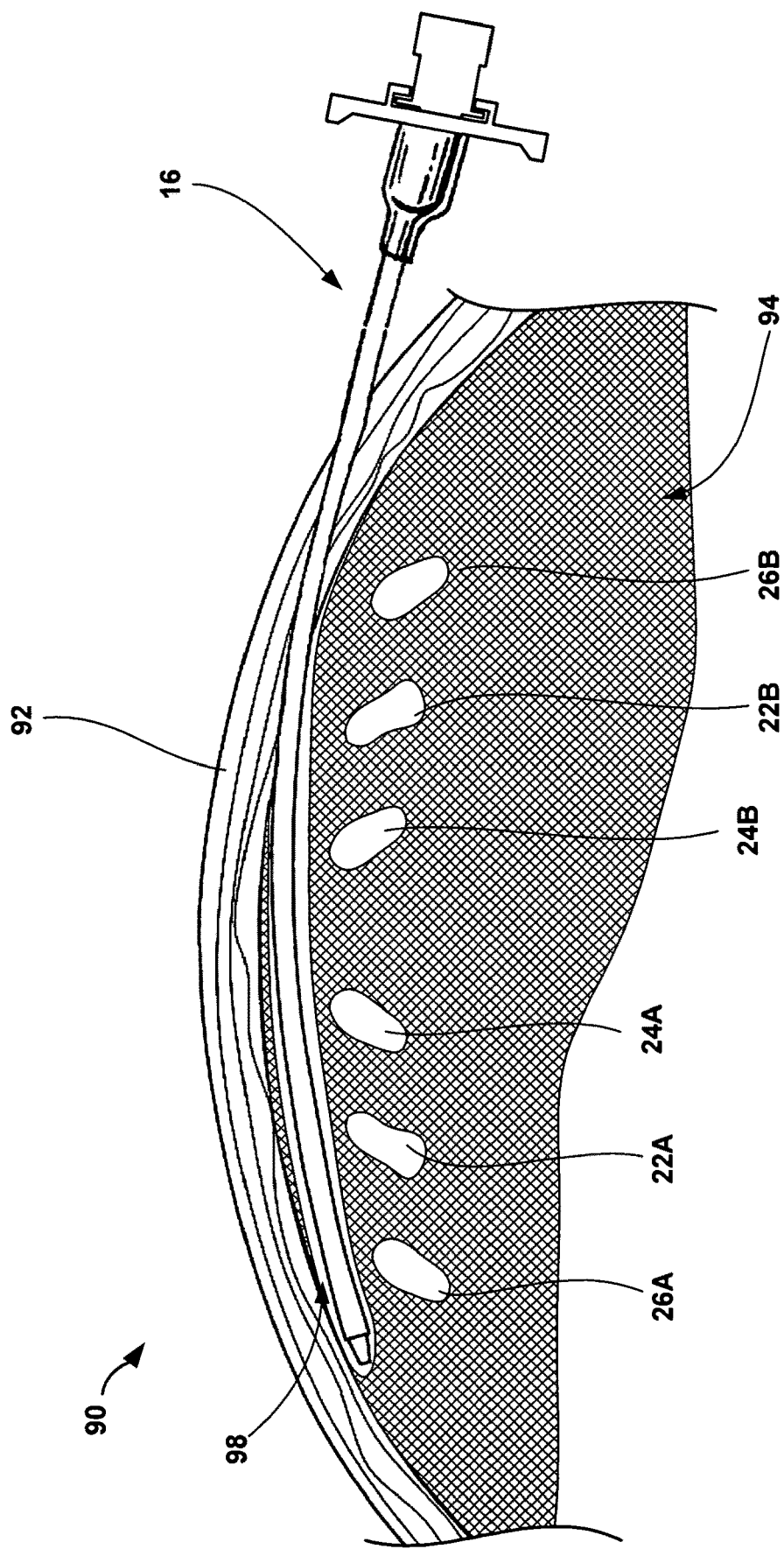
FIG. 13 is a conceptual cross-sectional view of an introducer implanted in subcutaneous tissue.

FIG. 13 is a conceptual top cross-sectional view of the back of neck 90 of patient 20. The back of neck 90 includes epidermis 92 and subcutaneous tissue 94 as well as lesser occipital nerves 22, greater occipital nerves 24, and third occipital nerves 26. Subcutaneous tissue 94 includes muscle and fascia with occipital nerves 22, 24, and 26 located within subcutaneous tissue 94 as previously described. FIG. 13 further shows introducer 16 implanted superficial to subcutaneous tissue 94, i.e., the muscle layer and fascia, but below epidermis 92.

Introducer 16 is configured to preferentially flex in one general direction over another direction. The clinician may orient introducer 16 (e.g., using marker 56, shown in FIG. 4) such that introducer 16 preferentially flexes toward occipital nerves 22, 24, and 26 and away from epidermis 92 of patient 20 in order to help prevent introducer 16 from inadvertently engaging with epidermis 92 and possibly extending through epidermis 92, which may cause patient discomfort.

In the illustrated example of FIG. 13, introducer 16 is curved along substantially its entire length to conform to the structure of the back of the neck of patient 20. However, as previously described, introducer 16 may be manipulated to form various shapes to conform to the back of the neck 90 or other anatomical structure. When inserted into patient 20 as shown, introducer 16 creates insertion path 98 within subcutaneous tissue 94. Medical lead 14 is typically implanted substantially along insertion path 98 when introducer 16 is removed from patient 20. However, prior to removing introducer 16, the clinician may position medial lead 14 and, more particularly, electrodes 28 relative to occipital nerves 22, 24, and 26 to provide stimulation to target site 18 using fluoroscopic guidance or another suitable means.

Figure 14:
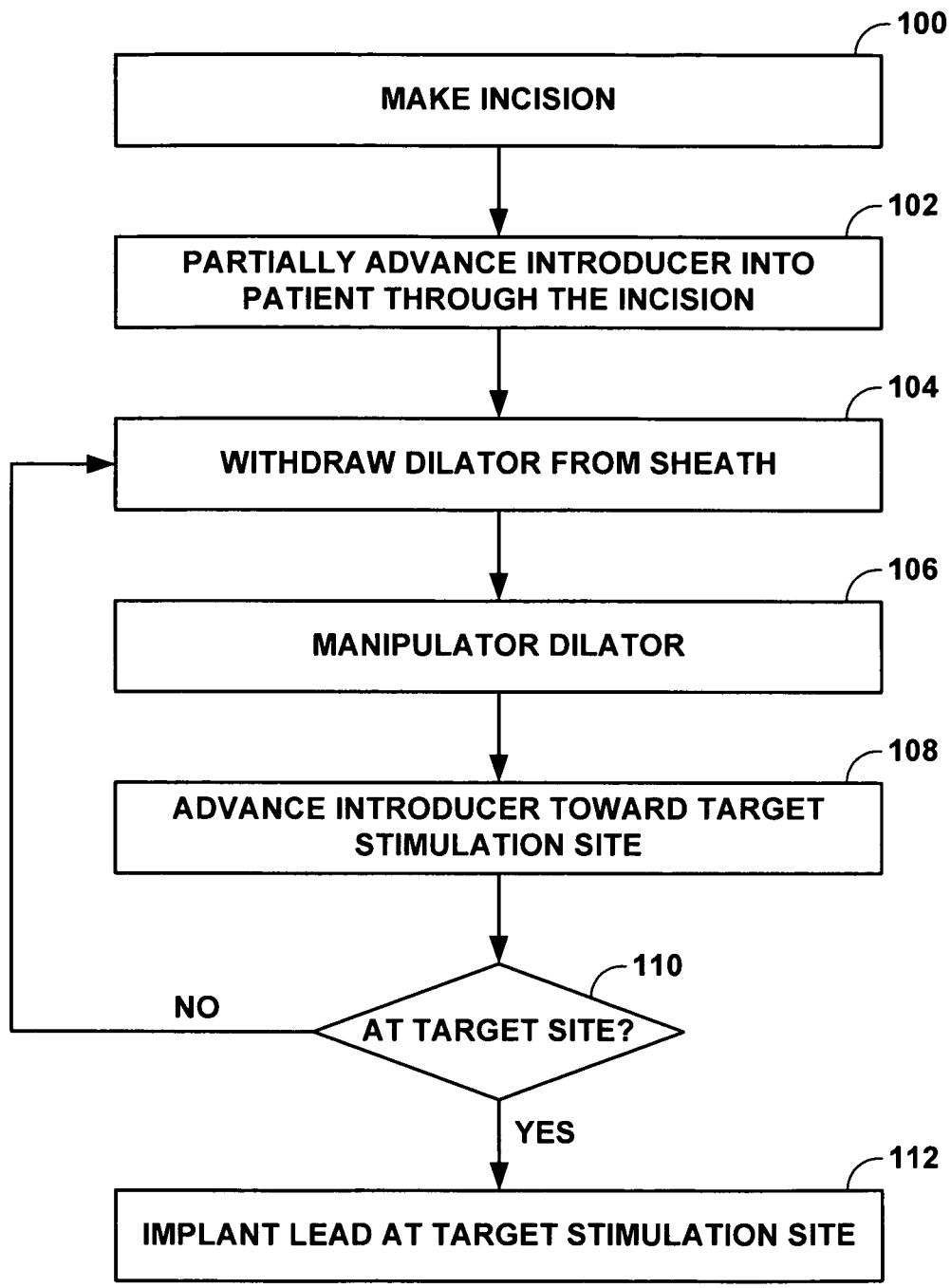
FIG. 14 is a flow chart illustrating an example method of implanting a therapy element into a patient using an introducer configured to preferentially flex in at least one direction over at least one other direction.

FIG. 14 is a flow chart illustrating an example method of using introducer 16 to facilitate implantation of medical lead 14 into patient 20. As previously described, introducer 16 is configured to bend more easily in at least one direction than at least one other direction. It should be understood that any configuration or implementation of introducer 16 described in FIGS. 5A-12B may be used to facilitate implantation of medical lead 14. Further, while implantation of lead 14 at target tissue site 18, i.e., proximate to at least one of occipital nerves 22, 24, and 26, is described, in other embodiments, introducer 16 may be used to facilitate implantation of lead 14 to any suitable target therapy site in patient 20, such as target tissue sites having an anatomical structure with an irregular shape or shape that may vary from patient to patient.

Initially, the clinician makes an incision (100) to ease introduction of introducer 16 into patient 20. In particular, the clinician makes a vertical skin incision approximately two centimeters in length in the back of the neck of patient 20 lateral to the midline of the spine at the level of the C1 vertebra. A local anesthetic may be used over the region of the incision to ensure the patient is alert an able to respond during the procedure. Fluoroscopy may be used to identify the C1 vertebra. Alternatively, a needle and/or guide wire may be used to define insertion path 98 (FIG. 13) prior to inserting introducer 16 into patient 20. In such an embodiment, introducer 16 may dilate an insertion path initially defined by a needle. An example of such a method is described in commonly-assigned U.S. Patent Application Publication No. 2008/0132979 by Martin T. Gerber, and entitled, "METHOD OF IMPLANTING AN OCCIPITAL STIMULATION LEAD," filed on Nov. 30, 2006, and commonly-assigned U.S. Pat. No. 6,847,849, which issued on Jan. 25, 2005 and is entitled, "MINIMALLY INVASIVE APPARATUS FOR IMPLANTING A SACRAL STIMULATION LEAD," each of which is incorporated herein by reference in its entirety.

The clinician then partially advances introducer 16 into patient 20 through the incision (102). The clinician may advance the introducer 16 into patient 20 under fluoroscopic guidance and/or using distance markers on introducer. Initially, introducer 16 may be straight over substantially its entire length. However, the back of the neck of patient 20 is curved. Thus, the clinician may insert introducer 16 superficial to the fascia and muscle layer but below the skin (scalp) and advance introducer 16. The clinician may advance introducer 16 until manipulation of introducer 16 is desirable to avoid damaging surrounding tissue. If manipulation of introducer 16 is desired, clinician may withdraw introducer 16 from patient. More specifically, the clinician may withdraw dilator 52 (104) while leaving sheath 50 implanted within patient 20. This may be accomplished by rotating dilator 52 so that interlocking members 59A can pass through the opening of interlocking members 59B.

When dilator 52 is withdrawn, the clinician may manipulate introducer 16, i.e., dilator 52, to bend introducer 16 in a predisposed direction (106). That is, the clinician may manually bend at least a portion of dilator 52 to conform to the back of the neck of patient 20 and curve away from the epidermis 92 or scalp of patient 20. In an alternate embodiment, dilator 52 may be manipulated (i.e., curved) while still disposed within patient 20.

The clinician may then re-insert dilator 52 into sheath 50 and advances introducer 16 toward target tissue site 18 (108). When the clinician re-inserts dilator 52 into sheath 50, the clinician may use orientation markers 56 as a reference to ensure that the curve of dilator 52 is properly oriented. The clinician then determines if introducer 16 has been advanced to target tissue site (110). This may be determined using fluoroscopy or by sending a test electrical signal via dilator 52 (which may be electrically conductive) and receiving patient feedback regarding the efficacy of the stimulation, any resulting side effects or similar feedback that indicates the relative location of distal end 16B of introducer 16 within patient 20. If introducer 16 has not been advanced to target tissue site 18, the introducer 16 may need to be manipulated to allow further advancement toward or retraction away from target tissue site 18 without damaging surround tissue. Accordingly, the clinician may repeat steps 104, 106, and 108 until determining that introducer 16 has been properly positioned proximate to target tissue site 18.

When introducer 16 has been advanced to target tissue site 18, the clinician may withdraw dilator 52 from sheath 50 and introduce lead 14 into sheath 50 in order to implant lead 14 proximate to target tissue site 18 (112). The clinician may utilize fluoroscopic guidance to accurately position electrodes 28 of lead 14 proximate to one or more of occipital nerves 22, 24, and 26 or alternatively, the clinician may send test electrical signals via electrodes 28 to determine whether electrodes 28 are positioned proximate to target tissue site 18. When the clinician is satisfied with the placement of lead 14, sheath 50 is removed leaving lead 14 implanted within patient 20. Fixation elements 38 of lead 14 may engage with surrounding tissue to locally fix electrodes 28 proximate to target stimulation side and substantially fix lead 14 to surrounding tissue.

Various embodiments of the invention have been described. These and other embodiments are within the scope of the following claims.

The invention claimed is:

1. An apparatus configured to facilitate implantation of a therapy element into tissue of a patient, the apparatus comprising:
   a dilator; and
   a sheath defining an inner lumen configured to interchangeably receive the dilator and the therapy element, wherein a first portion of the dilator is configured to preferentially flex in at least a first direction over at least a second direction that is different from the first direction, wherein a second portion of the dilator is configured to preferentially flex in the second direction, the dilator being configured to allow the first portion to flex in at least the first direction and the second portion to flex in the second direction at a same time, and wherein a cross-sectional shape of at least one of the first portion or the second portion of the dilator comprises an oval shape having a major axis and a minor axis, the oval shape having a first outer dimension along the major axis and a second outer dimension along the minor axis, wherein the first dimension is larger than the second dimension, and the at least one of the first portion or the second portion of the dilator being configured to preferentially flex about the major axis due to the respective oval shape.

2. The apparatus of claim 1, wherein the first portion of the dilator is configured to flex in the first direction to define a substantially curvilinear shape.

3. The apparatus of claim 1, wherein the first portion of the dilator is configured to flex in the first direction to substantially conform to a transverse contour of a neck of the patient.

4. The apparatus of claim 1, wherein when at least one of the first portion or the second portion of the dilator is in substantially non-flexed state, the at least one of the first portion or the second portion of the dilator is substantially axially aligned with a proximal end and a distal end of the dilator.

5. The apparatus of claim 1, wherein at least one of the first portion or the second portion of the dilator comprises an inner wall that comprises a first section having a first thickness and a second section having a second thickness that is greater than the first thickness, wherein the at least one of the first portion or the second portion is configured to preferentially flex along the first section.

6. The apparatus of claim 1, wherein the dilator comprises a proximal section and a distal section, at least one of the proximal or distal sections being inflexible, and at least one of the first portion or the second portion of the dilator being located between the proximal section and the distal section.

7. The apparatus of claim 1, further comprising one or more markers disposed on the dilator to indicate the first direction.

8. The apparatus of claim 1, further comprising one or more markers disposed on the sheath and configured to indicate a location of a distal end of the sheath relative to skin of the patient.

9. The apparatus of claim 1, wherein the sheath comprises a flexible material.

10. The apparatus of claim 1, wherein the therapy element comprises at least one of a lead body including one or more electrodes or a fluid delivery conduit.

11. The apparatus of claim 1, wherein the dilator has a length in a range of approximately two centimeters to approximately forty centimeters.

12. The apparatus of claim 11, wherein the dilator has a length in a range of approximately nine centimeters to approximately twenty centimeters.

13. The apparatus of claim 1, wherein the inner lumen has a diameter in a range of approximately one millimeter to approximately ten millimeters.

14. The apparatus of claim 1, wherein the dilator comprises a biocompatible material.

15. The apparatus of claim 1, wherein at least one of the first portion or the second portion of the dilator comprises a plurality of grooves.

16. A kit configured to facilitate implantation of a therapy element into a patient, the kit comprising:
a dilator comprising a first interlocking member; and
a sheath defining an inner lumen configured to interchangeably receive the dilator and the therapy element, the sheath comprising a second interlocking member,
wherein the first interlocking member is configured to interlock with the second interlocking member when the dilator is fully inserted in the sheath, and
wherein a first portion of the dilator is configured to preferentially flex in a first direction over at least a second direction that is different from the first direction, wherein a second portion of the dilator is configured to preferentially flex in the second direction, the dilator being configured to allow the first portion to flex in the first direction and the second portion to flex in the second direction at a same time, wherein a cross-sectional shape of at least one of the first portion or the second portion comprises an oval shape having a major axis and a minor axis, the oval shape having a first outer dimension along the major axis and a second outer dimension along the minor axis, wherein the first dimension is larger than the second dimension, and the at least one of the first portion or the second portion of the dilator being configured to preferentially flex about the major axis due to the respective oval shape.

17. The kit of claim 16, wherein the first portion of the dilator is configured to flex in the first direction to substantially conform to a transverse contour of a neck of the patient.

18. The kit of claim 16, wherein at least one of the first portion or the second portion of the dilator comprises a plurality of grooves.

19. The kit of claim 16, wherein at least one of the first portion or the second portion of the dilator comprises an inner wall comprising a first section having a first thickness and a second section having a second thickness that is greater than the first thickness.

20. A method comprising:
inserting an introducer into a patient, the introducer comprising:
a dilator; and
a sheath defining a lumen configured to interchangeably receive a therapy element and the dilator,
wherein a first portion of the dilator is configured to preferentially flex in at least a first direction over at least a second direction that is different from the first direction, and wherein a second portion of the dilator is configured to preferentially flex in the second direction, the dilator being configured to allow the first portion to flex in at least the first direction and the second portion to flex in the second direction at a same time, wherein a cross-sectional shape of the at least one of the first portion or the second portion of the dilator comprises an oval shape having a major axis and a minor axis, the oval shape having a first outer dimension along the major axis and a second outer dimension along the minor axis, wherein the first dimension is larger than the second dimension, and the at least one of the first portion or the second portion of the dilator being configured to preferentially flex about the major axis due to the respective oval shape;
advancing the introducer to a target tissue site within the patient; and
manipulating the first portion of the dilator to flex in the first direction substantially about the major axis.

21. The method of claim 20, further comprising introducing the therapy element into the lumen of the introducer.

22. The method of claim 21, wherein the therapy element comprises at least one of a lead body comprising one or more electrodes or a fluid delivery conduit.

23. The method of claim 20, further comprising at least partially withdrawing the dilator from the sheath prior to manipulating the first portion of dilator.

24. The method of claim 20, wherein manipulating the first portion of the dilator comprises manipulating the first portion to substantially define a curvilinear shape.

25. The method of claim 20, further comprising rotating the introducer such that the first portion of the dilator flexes substantially away from skin of the patient.

26. The method of claim 20, wherein the target tissue site is proximate to a peripheral nerve of the patient.

* * * * *